(12) United States Patent
Kensch

(10) Patent No.: US 9,040,277 B2
(45) Date of Patent: *May 26, 2015

(54) MANNANASE VARIANTS

(75) Inventor: Oliver Kensch, Köln (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/522,221

(22) PCT Filed: Nov. 24, 2010

(86) PCT No.: PCT/EP2010/007123
§ 371 (c)(1),
(2), (4) Date: Jul. 13, 2012

(87) PCT Pub. No.: WO2011/085747
PCT Pub. Date: Jul. 21, 2011

(65) Prior Publication Data
US 2012/0282239 A1 Nov. 8, 2012

Related U.S. Application Data

(60) Provisional application No. 61/294,684, filed on Jan. 13, 2010.

(51) Int. Cl.
| C12N 9/24 | (2006.01) |
|---|---|
| C12N 1/00 | (2006.01) |
| A61K 38/47 | (2006.01) |
| C11D 3/386 | (2006.01) |
| C12N 15/00 | (2006.01) |
| C09K 8/68 | (2006.01) |

(52) U.S. Cl.
CPC ......... *C12Y 302/01078* (2013.01); *C12N 15/00* (2013.01); *C09K 8/68* (2013.01); *C11D 3/38636* (2013.01); *C12N 9/2494* (2013.01)

(58) Field of Classification Search
CPC ......... C11D 3/38636; C09K 8/68; A23J 3/34; C12N 9/2494; C12N 15/00; C12Y 302/01078
USPC .............................. 424/94.61; 435/200, 254.3
See application file for complete search history.

(56) References Cited

U.S. PATENT DOCUMENTS

| 5,795,764 A | 8/1998 | Christgau et al. | |
|---|---|---|---|
| 7,846,705 B2 * | 12/2010 | Kensch et al. | ................ 435/200 |

FOREIGN PATENT DOCUMENTS

| GB | 9821198.0 | 11/1998 |
|---|---|---|
| WO | WO-03/012110 A1 | 2/2003 |
| WO | WO-2008009673 A2 | 1/2008 |
| WO | WO-2009108941 A2 | 9/2009 |

OTHER PUBLICATIONS

International Search Report for PCT/EP2010/007123 mailed May 12, 2011.
Altschul, S., et al., "Basic Local Alignment Search Tool", J. Mol. Biol., vol. 215, (1990), pp. 403-410.
Arisan-Atac, I., et al., "Purification, and characterization of a β-mannanase of *Trichoderma reesei* 0-30", Applied and Microbilogy Biotechnology, vol. 39, (1993), pp. 58-62.
Biely, P., et al., "Trichoderma and Gliocladium Volume 2", Taylor and Francis Ltd., (1998), pp. 25-47.
Livingstone, C., et al., "Protein sequence alignments: a strategy for the hierarchial analysis of residue conservation", Comput. Appl. Bosci., vol. 9, No. 6, (1993), pp. 745-756.
Morinaga, Y., et al., "Improvement of Oligonucleotide-Directed Site-Specific Mutagenesis Using Double-Stranded Plasmid DNA", Biotechnology, vol. 2, No. 19, (2006), pp. 636-639.
Nelson, R., et al., "A General Method of Site-Specific Mutagenesis Using a Modification of the *Thermus aquaticus* Polymerase Chain Reaction", Analytical Biochemistry, vol. 180, (1989), pp. 147-151.
Politz, O., et al., "A highly thermostable endo-(1,4)-β-mannanase from the marine bacterium *Rhodothermus marinus*", Appl. Microbiol. Biotechnol, vol. 53, (2000), pp. 715-721.
Schwartz, R.M., et al., "23 Matrices for Detecting Distant Relationships", Atlas of Protein Sequence and Structure, vol. 5, Supp. 3, (1978), pp. 353-358.
Smith, T., et al., "Comparison of Biosequences", Adavanced in Applied Mathematics, vol. 2, (1981), pp. 482-489.
Taylor, W. R., "The classification of amino acid conservation", J.Theor.Biol. vol. 119, No. 19, pp. 205-218.
Caldwell, R., et al., "Mutagenic PCR", vol. 13, (2007), pp. 136-140.
Gill, S., et al., "Calculation of Protein Extinction Coefficients from Amino Acid Seqence Data", Analytical Biochemistry, vol. 182, (1989), pp. 319-326.
Kensch: "Mannanase engineering for fibre degradation", Nov. 2008, XP002517050, Retrieved from the Internet: URL:http://www.direvo.com/media/SCM%20mannanase_081202.pdf [retrieved on Jan. 17, 2011].

* cited by examiner

*Primary Examiner* — Suzanne M Noakes
*Assistant Examiner* — Jae W Lee
(74) *Attorney, Agent, or Firm* — Marshall, Gerstein & Borun LLP

(57) ABSTRACT

The present disclosure provides novel mannanase variants which have an amino acid sequence that varies from that of the parent/wild type *Trichoderma reesei* mannanase, and which have one or more advantageous properties like improved thermo stability; temperature/activity profile; pH/activity profile; specific activity; and pH/protease-sensitivity. The novel mannanase variants are useful and used in alcohol fermentations processes and/or productions, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, as baking ingredients, for removal of biofilms and in delivery systems, for grain processing or for the processing of renewable resources intended for the production of biological fuels, and in the textile, oil drilling, cleaning, laundering, detergent, and cellulose fiber processing industries.

14 Claims, 11 Drawing Sheets

FIGURE 1

**Amino acid sequence of parent/wild-type *Trichoderma reesei* mannanase (SEQ ID NO: 1)**

```
  1  ASSFVTISGT QFNIDGKVGY FAGTNCYWCS FLTNHADVDS TFSHISSSGL KVVRVWGFND
 61  VNTQPSPGQI WFQKLSATGS TINTGADGLQ TLDYVVQSAE QHNLKLIIPF VNNWSDYGGI
121  NAYVNAFGGN ATTWYTNTAA QTQYRKYVQA VVSRYANSTA IFAWELGNEP RCNGCSTDVI
181  VQWATSVSQY VKSLDSNHLV TLGDEGLGLS TGDGAYPYTY GEGTDFAKNV QIKSLDFGTF
241  HLYPDSWGTN YTWGNGWIQT HAAACLAAGK PCVFEEYGAQ QNPCTNEAPW QTTSLTTRGM
301  GGDMFWQWGD TFANGAQSNS DPYTVWYNSS NWQCLVKNHV DAINGGTTTP PP
```

FIGURE 2

**Amino acid sequence of a *Trichoderma reesei* mannanase variant (SEQ ID NO: 2)**

```
  1  ASSFVTISGT QFNIDGKVGY FAGTNCYWCS FLTNHADVDS TFSHISSSGL KVVRVWGFND
 61  VNTQPSPGQI WFQKLSATGS TINTGADGLQ TLDYVVQSAE QHNLKLIIPF VNNWSDYGGI
121  NAYVNAFGGN ATTWYTNTAA QTQYRKYVQA VVSRYANSTA IFAWELGNEP RCNGCSTDVI
181  VQWATSVSQY VKSLDSNHLV SLGDEGFGLS TGDGAYPYTY GEGTDFAKNV QIKSLDFGTF
241  HLYPDSWGTN YTWGNGWIQT HAAACLAAGK PCVLEEYGAQ QNPCTNEAPW QTTSLTTRGM
301  GGDMFWQWGD TFANGAQSNS DPYTVWYNSS NWQCLVKNHV DAINGGTTTP PP
```

FIGURE 3

**Amino acid sequence of the *Trichoderma reesei* mannanase S3R variant (SEQ ID NO: 3)**

```
  1  ASRFVTISGT QFNIDGKVGY FAGTNCYWCS FLTNHADVDS TFSHISSSGL KVVRVWGFND
 61  VNTQPSPGQI WFQKLSATGS TINTGADGLQ TLDYVVQSAE QHNLKLIIPF VNNWSDYGGI
121  NAYVNAFGGN ATTWYTNTAA QTQYRKYVQA VVSRYANSTA IFAWELGNEP RCNGCSTDVI
181  VQWATSVSQY VKSLDSNHLV SLGDEGFGLS TGDGAYPYTY GEGTDFAKNV QIKSLDFGTF
241  HLYPDSWGTN YTWGNGWIQT HAAACLAAGK PCVLEEYGAQ QNPCTNEAPW QTTSLTTRGM
301  GGDMFWQWGD TFANGAQSNS DPYTVWYNSS NWQCLVKNHV DAINGGTTTP PP
```

(The R at position 3 is underlined.)

FIGURE 4

**Amino acid sequence of an improved *Trichoderma reesei* mannanase variant TM-1 (SEQ ID NO: 4)**

```
  1  ASRFVTISGT QFNIDGKVGY FAGTNCYWCS FLTNHADVDS TFSHISSSGL KVVRVWGFND
 61  VNTQPPPGQI WFQKLSATGS TINTGADGLQ TLDYVVQSAE QHNLKLIIPF VNNWSDYGGI
121  NAYVNAFGGN ATTWYTNTAA QTQYRKYVQA VVSRYANSTA IFAWELGNEP RCNGCSTDVI
181  VQWATSVSQY VKSLDSNHLV SLGDEGFGLS TGDGTYPYTY GEGTDFAKNV QIKSLDFGTF
241  HLYPDSWGTN YTWGNGWIRT HAAACLAAGK PCVLEEYGAQ QNPCTNEAPW QTTSLTTRGM
301  GGDMFWQWGD TFANGAQSNS DPYTVWYNSS NWQCLVKNHV DAINGGTTTP PP
```

FIGURE 5

Nucleic acid sequence of the mannanase variant TM-1 (SEQ ID NO: 5)

```
   1  GCTTCTAGAT TTGTAACCAT ATCCGGCACC CAATTCAACA TCGATGGCAA AGTAGGCTAC
  61  TTTGCGGGCA CCAACTGCTA CTGGTGCTCG TTCCTGACCA ACCACGCCGA CGTTGATTCC
 121  ACCTTTAGCC ACATCTCTTC CTCTGGCCTC AAGGTAGTCC GTGTATGGGG CTTCAACGAC
 181  GTCAACACGC AGCCCCCTCC CGGCCAGATC TGGTTCCAGA AGCTGTCCGC TACGGGGTCT
 241  ACGATCAACA CGGGAGCTGA TGGGCTGCAG ACTCTCGACT ACGTAGTCCA ATCAGCCGAG
 301  CAGCACAACC TCAAGCTCAT CATCCCGTTC GTCAACAACT GGAGCGACTA CGGCGGGATA
 361  AACGCCTATG TCAACGCCTT TGGCGGCAAT GCGACCACCT GGTACACTAA CACGGCCGCG
 421  CAAACTCAGT ACCGCAAGTA CGTCCAGGCC GTCGTCAGCC GCTACGCAAA CTCGACGGCC
 481  ATCTTTGCGT GGGAGCTGGG CAACGAGCCT CGCTGCAACG GGTGCAGTAC TGATGTGATT
 541  GTTCAGTGGG CGACGAGTGT GTCCCAATAT GTCAAGTCAC TTGATTCGAA CCATCTCGTG
 601  TCTCTTGGAG ACGAGGGATT CGGTCTCAGT ACTGGAGACG GCACTTATCC GTATACTTAC
 661  GGCGAGGGCA CTGATTTTGC CAAGAATGTA CAAATCAAGT CGCTTGACTT TGGTACTTTC
 721  CACCTCTATC CGGACTCTTG GGAACAAAC TACACTTGGG GCAATGGCTG GATTAGAACT
 781  CATGCCGCCG CTTGTTTAGC AGCAGGCAAA CCTTGCGTGC TTGAAGAATA CGGCGCACAA
 841  CAAAATCCCT GCACCAACGA GGCACCCTGG CAAACAACCT CTCTCACGAC TCGCGGCATG
 901  GGTGGCGACA TGTTTTGGCA GTGGGGAGAC ACTTTTGCCA ACGGTGCCCA GTCGAACAGT
 961  GACCCGTACA CCGTCTGGTA CAACTCATCG AACTGGCAAT GCTTGGTCAA GAACCACGTT
1021  GATGCTATTA ACGGCGGTAC AACCACTCCT CCTCCC
```

FIGURE 6

**Amino acid sequence of an improved *Trichoderma reesei* mannanase variant TM-100 (SEQ ID NO: 6)**

```
  1   ASRFVTISGT QFNIDGKVGY FAGTNCYWCS YLTNHADVDS TFSHISSSGL KVVRVWGFND
 61   VNTQPPPGQI WFQKLSATGS TINTGADGLQ TLDYVVRSAE QHNLKLIIPF VNYWSDYGGI
121   NAYVNAFGGN ATTWYTNTAA QTQYRKYVQA VVSRYANSTA IFAWELGNEP RCHGCSTDVI
181   HQWATSVSQY VKSLDSNHLV SLGDEGFGLS TGDGTYPYTY GEGTDFAKNV QIKSLDFGTF
241   HLYPDSWGTN YTWGNGWIRT HAAACLAAGK PCVLEEYGAR QDPCTNEAPW QTTSLTTRGM
301   GGDMFWQWGD TFANGAQSNS DPYTVWYNSS SWQCLVKNHV DAINGGTTTP PPHHHHHH
```

FIGURE 7

**Amino acid sequence of an improved *Trichoderma reesei* mannanase variant TM-108 (SEQ ID NO: 7)**

```
  1  ASRFVTISGT QFNIDGKVGY FAGTNCYWCS FLTNHADVDS TFSHISSSGL KVVRVWGFND
 61  VNTQPPPGQI WFQKLSATGS TINTGADGLQ TLDYVVQSAE QHNLKLIIPF VNYWSDYGGI
121  NAYVNAFGGN ATTWYTNTAA QTQYRKYVQA VVSRYANSTA IFAWELGNEP RCHGCSTDVI
181  HQWATSVSQY VKSLDSNHLV SLGDEGFGLS TGDGTYPYTY GEGTDFAKNV QIKSLDFGTF
241  HLYPDSWGTN YTWGNGWIRT HAAACLAAGK PCVLEEYGAQ QNPCTNEAPW QTTSLTTRGM
301  GGDMFWQWGD TFANGAQSNS DPYTVWYNSS NWQCLVKNHV DAINGGTTTP PPHHHHHH
```

FIGURE 8

**Amino acid sequence of an improved *Trichoderma reesei* mannanase variant TM-CBD-148 (SEQ ID NO: 8)**

```
  1   ASRFVTISGT QFNIDGKVGY FAGTNCYWCS YLTNHADVDS TFSHISSSGL KVVRVWGFND
 61   VNTQPPPGQI WFQKLSATGS TINTGADGLQ TLDYVVRSAE QHNLKLIIPF VNYWSDYGGI
121   NAYVNAFGGN ATTWYTNTAA QTQYRKYVQA VVSRYANSTA IFAWELGNEP RCHGCSTDVI
181   HQWATSVSQY VKSLDSNHLV SLGDEGFGLS TGDGTYPYTY GEGTDFAKNV QIKSLDFGTF
241   HLYPDSWGTN YTWGNGWIRT HAAACLAAGK PCVLEEYGAR QDPCTNEAPW QTTSLTTRGM
301   GGDMFWQWGD TFANGAQSNS DPYTVWYNSS NWQCLVKNHV DAINGGTTTP PPVSSTTTTS
361   SRTSSTPPPP GGSCSPLYGQ CGGSGYTGPT CCAQGTCIYS NYWYSQCLNT
```

FIGURE 9

**Amino acid sequence of an improved *Trichoderma reesei* mannanase variant TM-144 (SEQ ID NO: 9)**

```
  1  ASRFVTISGT QFNIDGKVGY FAGTNCYWCS FLTNHADVDS TFSHISSSGL KVVRVWGFND
 61  VNTQPPPGQI WFQKLSATGS TINTGADGLQ TLDYVVQSAE QHNLKLIIPF VNNWSDYGGI
121  NAYVNAFGGN ATTWYTNTAA QTQYRKYVQA VVSRYANSTA IFAWELGNEP RCNGCSTDVI
181  HQWATSVSQY VKSLDSNHLV SLGDEGFGLS TGDGTYPYTY GEGTDFAKNV QIKSLDFGTF
241  HLYPDSWGTN YTWGNGWIRT HAAACLAAGK PCVLEEYGAQ QNPCTNEAPW QTTSLTTRGM
301  GGDMFWQWGD TFANGAQSNS DPYTVWYNSS NWQCLVKNHV DAINGGTTTP PPHHHHHH
```

Comparison of the wild type *Trichoderma reesei* mannanase and the S3R-variant with respect to thermal stability and activity.

FIGURE 11

Amino acid sequence of a CBD (SEQ ID NO: 10)

Val Ser Ser Thr Thr Thr Thr Ser Ser Arg Thr Ser Ser Thr Pro Pro Pro Pro Gly Gly Ser Cys
Ser Pro Leu Tyr Gly Gln Cys Gly Gly Ser Gly Tyr Thr Gly Pro Thr Cys Cys Ala Gln Gly Thr
Cys Ile Tyr Ser Asn Tyr Trp Tyr Ser Gln Cys Leu Asn Thr

SEQUENCE LISTING

<160> NUMBER OF SEQ ID NOS: 10

<210> SEQ ID NO 1
<211> LENGTH: 352
<212> TYPE: PRT
<213> ORGANISM: Trichoderma reesei

<400> SEQUENCE: 1

Ala Ser Ser Phe Val Thr Ile Ser Gly Thr Gln Phe Asn Ile Asp Gly

```
  1               5                  10                 15
Lys Val Gly Tyr Phe Ala Gly Thr Asn Cys Tyr Trp Cys Ser Phe Leu
                20                 25                 30

Thr Asn His Ala Asp Val Asp Ser Thr Phe Ser His Ile Ser Ser Ser
                35                 40                 45

Gly Leu Lys Val Val Arg Val Trp Gly Phe Asn Asp Val Asn Thr Gln
 50                 55                 60

Pro Ser Pro Gly Gln Ile Trp Phe Gln Lys Leu Ser Ala Thr Gly Ser
 65                 70                 75                 80

Thr Ile Asn Thr Gly Ala Asp Gly Leu Gln Thr Leu Asp Tyr Val Val
                85                 90                 95

Gln Ser Ala Glu Gln His Asn Leu Lys Leu Ile Ile Pro Phe Val Asn
                100                105                110

Asn Trp Ser Asp Tyr Gly Gly Ile Asn Ala Tyr Val Asn Ala Phe Gly
                115                120                125

Gly Asn Ala Thr Thr Trp Tyr Thr Asn Thr Ala Ala Gln Thr Gln Tyr
                130                135                140

Arg Lys Tyr Val Gln Ala Val Val Ser Arg Tyr Ala Asn Ser Thr Ala
145                150                155                160

Ile Phe Ala Trp Glu Leu Gly Asn Glu Pro Arg Cys Asn Gly Cys Ser
                165                170                175

Thr Asp Val Ile Val Gln Trp Ala Thr Ser Val Ser Gln Tyr Val Lys
                180                185                190

Ser Leu Asp Ser Asn His Leu Val Thr Leu Gly Asp Glu Gly Leu Gly
                195                200                205

Leu Ser Thr Gly Asp Gly Ala Tyr Pro Tyr Thr Tyr Gly Glu Gly Thr
 210                215                220

Asp Phe Ala Lys Asn Val Gln Ile Lys Ser Leu Asp Phe Gly Thr Phe
225                230                235                240

His Leu Tyr Pro Asp Ser Trp Gly Thr Asn Tyr Thr Trp Gly Asn Gly
                245                250                255

Trp Ile Gln Thr His Ala Ala Cys Leu Ala Ala Gly Lys Pro Cys
                260                265                270

Val Phe Glu Glu Tyr Gly Ala Gln Gln Asn Pro Cys Thr Asn Glu Ala
                275                280                285

Pro Trp Gln Thr Thr Ser Leu Thr Thr Arg Gly Met Gly Gly Asp Met
                290                295                300

Phe Trp Gln Trp Gly Asp Thr Phe Ala Asn Gly Ala Gln Ser Asn Ser
305                310                315                320

Asp Pro Tyr Thr Val Trp Tyr Asn Ser Ser Asn Trp Gln Cys Leu Val
                325                330                335

Lys Asn His Val Asp Ala Ile Asn Gly Gly Thr Thr Thr Pro Pro Pro
                340                345                350

<210> SEQ ID NO 2
<211> LENGTH: 352
<212> TYPE: PRT
<213> ORGANISM: Artificial Sequence
<220> FEATURE:
<223> OTHER INFORMATION: Mannanase variant

<400> SEQUENCE: 2

Ala Ser Ser Phe Val Thr Ile Ser Gly Thr Gln Phe Asn Ile Asp Gly
 1               5                  10                 15

Lys Val Gly Tyr Phe Ala Gly Thr Asn Cys Tyr Trp Cys Ser Phe Leu
```

```
                20                  25                  30
Thr Asn His Ala Asp Val Asp Ser Thr Phe Ser His Ile Ser Ser Ser
            35                  40                  45
Gly Leu Lys Val Val Arg Val Trp Gly Phe Asn Asp Val Asn Thr Gln
 50                  55                  60
Pro Ser Pro Gly Gln Ile Trp Phe Gln Lys Leu Ser Ala Thr Gly Ser
 65                  70                  75                  80
Thr Ile Asn Thr Gly Ala Asp Gly Leu Gln Thr Leu Asp Tyr Val Val
                85                  90                  95
Gln Ser Ala Glu Gln His Asn Leu Lys Leu Ile Ile Pro Phe Val Asn
            100                 105                 110
Asn Trp Ser Asp Tyr Gly Gly Ile Asn Ala Tyr Val Asn Ala Phe Gly
            115                 120                 125
Gly Asn Ala Thr Thr Trp Tyr Thr Asn Thr Ala Ala Gln Thr Gln Tyr
            130                 135                 140
Arg Lys Tyr Val Gln Ala Val Val Ser Arg Tyr Ala Asn Ser Thr Ala
145                 150                 155                 160
Ile Phe Ala Trp Glu Leu Gly Asn Glu Pro Arg Cys Asn Gly Cys Ser
                165                 170                 175
Thr Asp Val Ile Val Gln Trp Ala Thr Ser Val Ser Gln Tyr Val Lys
            180                 185                 190
Ser Leu Asp Ser Asn His Leu Val Ser Leu Gly Asp Glu Gly Phe Gly
            195                 200                 205
Leu Ser Thr Gly Asp Gly Ala Tyr Pro Tyr Thr Tyr Gly Glu Gly Thr
            210                 215                 220
Asp Phe Ala Lys Asn Val Gln Ile Lys Ser Leu Asp Phe Gly Thr Phe
225                 230                 235                 240
His Leu Tyr Pro Asp Ser Trp Gly Thr Asn Tyr Thr Trp Gly Asn Gly
                245                 250                 255
Trp Ile Gln Thr His Ala Ala Ala Cys Leu Ala Ala Gly Lys Pro Cys
            260                 265                 270
Val Leu Glu Glu Tyr Gly Ala Gln Gln Asn Pro Cys Thr Asn Glu Ala
            275                 280                 285
Pro Trp Gln Thr Thr Ser Leu Thr Thr Arg Gly Met Gly Gly Asp Met
            290                 295                 300
Phe Trp Gln Trp Gly Asp Thr Phe Ala Asn Gly Ala Gln Ser Asn Ser
305                 310                 315                 320
Asp Pro Tyr Thr Val Trp Tyr Asn Ser Ser Asn Trp Gln Cys Leu Val
                325                 330                 335
Lys Asn His Val Asp Ala Ile Asn Gly Gly Thr Thr Pro Pro Pro
            340                 345                 350

<210> SEQ ID NO 3
<211> LENGTH: 352
<212> TYPE: PRT
<213> ORGANISM: Artificial Sequence
<220> FEATURE:
<223> OTHER INFORMATION: S3R mannase variant

<400> SEQUENCE: 3

Ala Ser Arg Phe Val Thr Ile Ser Gly Thr Gln Phe Asn Ile Asp Gly
 1               5                  10                  15
Lys Val Gly Tyr Phe Ala Gly Thr Asn Cys Tyr Trp Cys Ser Phe Leu
                20                  25                  30
Thr Asn His Ala Asp Val Asp Ser Thr Phe Ser His Ile Ser Ser Ser
```

```
            35                  40                  45
Gly Leu Lys Val Val Arg Val Trp Gly Phe Asn Asp Val Asn Thr Gln
 50                  55                  60

Pro Ser Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
                85                  90                  95

Gln Ser Ala Glu Gln His Asn Leu Lys Leu Ile Ile Pro Phe Val Asn
            100                 105                 110

Asn Trp Ser Asp Tyr Gly Gly Ile Asn Ala Tyr Val Asn Ala Phe Gly
        115                 120                 125

Gly Asn Ala Thr Thr Trp Tyr Thr Asn Thr Ala Ala Gln Thr Gln Tyr
    130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys Asn Gly Cys Ser
                165                 170                 175

Thr Asp Val Ile Val Gln Trp Ala Thr Ser Val Ser Gln Tyr Val Lys
            180                 185                 190

Ser Leu Asp Ser Asn His Leu Val Ser Leu Gly Asp Glu Gly Phe Gly
        195                 200                 205

Leu Ser Thr Gly Asp Gly Ala Tyr Pro Tyr Thr Tyr Gly Glu Gly Thr
    210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
                245                 250                 255

Trp Ile Gln Thr His Ala Ala Cys Leu Ala Ala Gly Lys Pro Cys
            260                 265                 270

Val Leu Glu Glu Tyr Gly Ala Gln Gln Asn Pro Cys Thr Asn Glu Ala
        275                 280                 285

Pro Trp Gln Thr Thr Ser Leu Thr Thr Arg Gly Met Gly Gly Asp Met
    290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Trp Gln Cys Leu Val
                325                 330                 335

Lys Asn His Val Asp Ala Ile Asn Gly Gly Thr Thr Thr Pro Pro Pro
            340                 345                 350

<210> SEQ ID NO 4
<211> LENGTH: 352
<212> TYPE: PRT
<213> ORGANISM: Artificial Sequence
<220> FEATURE:
<223> OTHER INFORMATION: mannase TM-1 variant

<400> SEQUENCE: 4

Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
                20                  25                  30

Thr Asn His Ala Asp Val Asp Ser Thr Phe Ser His Ile Ser Ser Ser
            35                  40                  45

Gly Leu Lys Val Val Arg Val Trp Gly Phe Asn Asp Val Asn Thr Gln
```

```
                  50                  55                  60
       Pro Pro Pro Gly Gln Ile Trp Phe Gln Lys Leu Ser Ala Thr Gly Ser
       65                  70                  75                  80

Thr Ile Asn Thr Gly Ala Asp Gly Leu Gln Thr Leu Asp Tyr Val Val
                           85                  90                  95

Gln Ser Ala Glu Gln His Asn Leu Lys Leu Ile Ile Pro Phe Val Asn
                       100                 105                 110

Asn Trp Ser Asp Tyr Gly Gly Ile Asn Ala Tyr Val Asn Ala Phe Gly
                   115                 120                 125

Gly Asn Ala Thr Thr Trp Tyr Thr Asn Thr Ala Ala Gln Thr Gln Tyr
               130                 135                 140

Arg Lys Tyr Val Gln Ala Val Val Ser Arg Tyr Ala Asn Ser Thr Ala
       145                 150                 155                 160

Ile Phe Ala Trp Glu Leu Gly Asn Glu Pro Arg Cys Asn Gly Cys Ser
                           165                 170                 175

Thr Asp Val Ile Val Gln Trp Ala Thr Ser Val Ser Gln Tyr Val Lys
                       180                 185                 190

Ser Leu Asp Ser Asn His Leu Val Ser Leu Gly Asp Glu Gly Phe Gly
                   195                 200                 205

Leu Ser Thr Gly Asp Gly Thr Tyr Pro Tyr Thr Tyr Gly Glu Gly Thr
               210                 215                 220

Asp Phe Ala Lys Asn Val Gln Ile Lys Ser Leu Asp Phe Gly Thr Phe
       225                 230                 235                 240

His Leu Tyr Pro Asp Ser Trp Gly Thr Asn Tyr Thr Trp Gly Asn Gly
                           245                 250                 255

Trp Ile Arg Thr His Ala Ala Ala Cys Leu Ala Ala Gly Lys Pro Cys
                       260                 265                 270

Val Leu Glu Glu Tyr Gly Ala Gln Gln Asn Pro Cys Thr Asn Glu Ala
                   275                 280                 285

Pro Trp Gln Thr Thr Ser Leu Thr Thr Arg Gly Met Gly Gly Asp Met
               290                 295                 300

Phe Trp Gln Trp Gly Asp Thr Phe Ala Asn Gly Ala Gln Ser Asn Ser
       305                 310                 315                 320

Asp Pro Tyr Thr Val Trp Tyr Asn Ser Ser Asn Trp Gln Cys Leu Val
                           325                 330                 335

Lys Asn His Val Asp Ala Ile Asn Gly Gly Thr Thr Thr Pro Pro Pro
                       340                 345                 350

<210> SEQ ID NO 5
<211> LENGTH: 1056
<212> TYPE: DNA
<213> ORGANISM: Artificial Sequence
<220> FEATURE:
<223> OTHER INFORMATION: mannanase TM-1 variant na

<400> SEQUENCE: 5
gcttctagat tgtaaccat  atccggcacc caattcaaca tcgatggcaa agtaggctac        60
tttgcgggca ccaactgcta ctggtgctcg ttcctgacca ccacgccga  cgttgattcc       120 acctttagcc acatctcttc ctctggcctc aaggtagtcc gtgtatgggg cttcaacgac       180
gtcaacacgc agccccctcc cggccagatc tggttccaga agctgtccgc tacgggtct        240 acgatcaaca cgggagctga tgggctgcag actctcgact acgtagtcca atcagccgag       300
cagcacaacc tcaagctcat catcccgttc gtcaacaact ggagcgacta cggcgggata       360
aacgcctatg tcaacgcctt tggcggcaat gcgaccacct ggtacactaa cacggccgcg       420
```

```
caaactcagt accgcaagta cgtccaggcc gtcgtcagcc gctacgcaaa ctcgacggcc    480
atctttgcgt gggagctggg caacgagcct cgctgcaacg ggtgcagtac tgatgtgatt    540
gttcagtggg cgacgagtgt gtcccaatat gtcaagtcac ttgattcgaa ccatctcgtg    600
tctcttggag acgagggatt cggtctcagt actggaacg gcacttatcc gtatacttac    660
ggcgagggca ctgattttgc caagaatgta caaatcaagt cgcttgactt tggtactttc    720
cacctctatc cggactcttg ggaacaaac tacacttggg gcaatggctg gattagaact    780
catgccgccg cttgtttagc agcaggcaaa ccttgcgtgc ttgaagaata cggcgcacaa    840
caaaatccct gcaccaacga ggcaccctgg caaacaacct ctctcacgac tcgcggcatg    900
ggtggcgaca tgttttggca gtggggagac acttttgcca acggtgccca gtcgaacagt    960
gacccgtaca ccgtctggta caactcatcg aactggcaat gcttggtcaa gaaccacgtt   1020
gatgctatta acggcggtac aaccactcct cctccc                             1056
```

<210> SEQ ID NO 6  
<211> LENGTH: 358  
<212> TYPE: PRT  
<213> ORGANISM: Artificial Sequence  
<220> FEATURE:  
<223> OTHER INFORMATION: mannanase variant TM-100 aa

<400> SEQUENCE: 6

```
Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Tyr Leu
            20                  25                  30

Thr Asn His Ala Asp Val Asp Ser Thr Phe Ser His Ile Ser Ser Ser
        35                  40                  45

Gly Leu Lys Val Val Arg Val Trp Gly Phe Asn Asp Val Asn Thr Gln
    50                  55                  60

Pro Pro Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
                85                  90                  95

Arg Ser Ala Glu Gln His Asn Leu Lys Leu Ile Ile Pro Phe Val Asn
            100                 105                 110

Tyr Trp Ser Asp Tyr Gly Gly Ile Asn Ala Tyr Val Asn Ala Phe Gly
        115                 120                 125

Gly Asn Ala Thr Thr Trp Tyr Thr Asn Thr Ala Ala Gln Thr Gln Tyr
    130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys His Gly Cys Ser
                165                 170                 175

Thr Asp Val Ile His Gln Trp Ala Thr Ser Val Ser Gln Tyr Val Lys
            180                 185                 190

Ser Leu Asp Ser Asn His Leu Val Ser Leu Gly Asp Glu Gly Phe Gly
        195                 200                 205

Leu Ser Thr Gly Asp Gly Thr Tyr Pro Tyr Thr Tyr Gly Glu Gly Thr
    210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
```

```
                        245                 250                 255
Trp Ile Arg Thr His Ala Ala Cys Leu Ala Ala Gly Lys Pro Cys
            260                 265                 270

Val Leu Glu Glu Tyr Gly Ala Arg Gln Asp Pro Cys Thr Asn Glu Ala
            275                 280                 285

Pro Trp Gln Thr Thr Ser Leu Thr Thr Arg Gly Met Gly Gly Asp Met
            290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Trp Gln Cys Leu Val
            325                 330                 335

Lys Asn His Val Asp Ala Ile Asn Gly Gly Thr Thr Pro Pro Pro
            340                 345                 350

His His His His His His
            355
```

<210> SEQ ID NO 7
<211> LENGTH: 358
<212> TYPE: PRT
<213> ORGANISM: Artificial Sequence
<220> FEATURE:
<223> OTHER INFORMATION: mannanase variant TM-108 aa

<400> SEQUENCE: 7

```
Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
            20                  25                  30

Thr Asn His Ala Asp Val Asp Ser Thr Phe Ser His Ile Ser Ser Ser
            35                  40                  45

Gly Leu Lys Val Val Arg Val Trp Gly Phe Asn Asp Val Asn Thr Gln
50                  55                  60

Pro Pro Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
            85                  90                  95

Gln Ser Ala Glu Gln His Asn Leu Lys Leu Ile Ile Pro Phe Val Asn
            100                 105                 110

Tyr Trp Ser Asp Tyr Gly Gly Ile Asn Ala Tyr Val Asn Ala Phe Gly
            115                 120                 125

Gly Asn Ala Thr Thr Trp Tyr Thr Asn Thr Ala Ala Gln Thr Gln Tyr
130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys His Gly Cys Ser
            165                 170                 175

Thr Asp Val Ile His Gln Trp Ala Thr Ser Val Ser Gln Tyr Val Lys
            180                 185                 190

Ser Leu Asp Ser Asn His Leu Val Ser Leu Gly Asp Glu Gly Phe Gly
            195                 200                 205

Leu Ser Thr Gly Asp Gly Thr Tyr Pro Tyr Thr Tyr Gly Glu Gly Thr
            210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
```

-continued

```
                        245                 250                 255
Trp Ile Arg Thr His Ala Ala Ala Cys Leu Ala Ala Gly Lys Pro Cys
            260                 265                 270

Val Leu Glu Glu Tyr Gly Ala Gln Gln Asn Pro Cys Thr Asn Glu Ala
        275                 280                 285

Pro Trp Gln Thr Thr Ser Leu Thr Thr Arg Gly Met Gly Gly Asp Met
    290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Asn Trp Gln Cys Leu Val
            325                 330                 335

Lys Asn His Val Asp Ala Ile Asn Gly Gly Thr Thr Pro Pro
        340                 345                 350

His His His His His His
        355
```

<210> SEQ ID NO 8
<211> LENGTH: 410
<212> TYPE: PRT
<213> ORGANISM: Artificial Sequence
<220> FEATURE:
<223> OTHER INFORMATION: mannanase variant TM-CBD-148 aa

<400> SEQUENCE: 8

```
Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Tyr Leu
            20                  25                  30

Thr Asn His Ala Asp Val Asp Ser Thr Phe Ser His Ile Ser Ser Ser
        35                  40                  45

Gly Leu Lys Val Val Arg Val Trp Gly Phe Asn Asp Val Asn Thr Gln
    50                  55                  60

Pro Pro Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
            85                  90                  95

Arg Ser Ala Glu Gln His Asn Leu Lys Leu Ile Ile Pro Phe Val Asn
        100                 105                 110

Tyr Trp Ser Asp Tyr Gly Gly Ile Asn Ala Tyr Val Asn Ala Phe Gly
    115                 120                 125

Gly Asn Ala Thr Thr Trp Tyr Thr Asn Thr Ala Ala Gln Thr Gln Tyr
130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys His Gly Cys Ser
            165                 170                 175

Thr Asp Val Ile His Gln Trp Ala Thr Ser Val Ser Gln Tyr Val Lys
        180                 185                 190

Ser Leu Asp Ser Asn His Leu Val Ser Leu Gly Asp Glu Gly Phe Gly
    195                 200                 205

Leu Ser Thr Gly Asp Gly Thr Tyr Pro Tyr Thr Tyr Gly Glu Gly Thr
    210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
```

```
            245                 250                 255
Trp Ile Arg Thr His Ala Ala Ala Cys Leu Ala Ala Gly Lys Pro Cys
            260                 265                 270

Val Leu Glu Glu Tyr Gly Ala Arg Gln Asp Pro Cys Thr Asn Glu Ala
            275                 280                 285

Pro Trp Gln Thr Thr Ser Leu Thr Thr Arg Gly Met Gly Gly Asp Met
            290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Asn Trp Gln Cys Leu Val
                325                 330                 335

Lys Asn His Val Asp Ala Ile Asn Gly Gly Thr Thr Pro Pro Pro Pro
                340                 345                 350

Val Ser Ser Thr Thr Thr Thr Ser Ser Arg Thr Ser Thr Ser Pro Pro
                355                 360                 365

Pro Pro Gly Gly Ser Cys Ser Pro Leu Tyr Gly Gln Cys Gly Gly Ser
            370                 375                 380

Gly Tyr Thr Gly Pro Thr Cys Cys Ala Gln Gly Thr Cys Ile Tyr Ser
385                 390                 395                 400

Asn Tyr Trp Tyr Ser Gln Cys Leu Asn Thr
                405                 410

<210> SEQ ID NO 9
<211> LENGTH: 358
<212> TYPE: PRT
<213> ORGANISM: Artificial Sequence
<220> FEATURE:
<223> OTHER INFORMATION: mannanase variant TM-144 aa

<400> SEQUENCE: 9

Ala Ser Arg Phe Val Thr Ile Ser Gly Thr Gln Phe Asn Ile Asp Gly
1               5                   10                  15

Lys Val Gly Tyr Phe Ala Gly Thr Asn Cys Tyr Trp Cys Ser Phe Leu
            20                  25                  30

Thr Asn His Ala Asp Val Asp Ser Thr Phe Ser His Ile Ser Ser Ser
            35                  40                  45

Gly Leu Lys Val Val Arg Val Trp Gly Phe Asn Asp Val Asn Thr Gln
    50                  55                  60

Pro Pro Pro Gly Gln Ile Trp Phe Gln Lys Leu Ser Ala Thr Gly Ser
65                  70                  75                  80

Thr Ile Asn Thr Gly Ala Asp Gly Leu Gln Thr Leu Asp Tyr Val Val
                85                  90                  95

Gln Ser Ala Glu Gln His Asn Leu Lys Leu Ile Ile Pro Phe Val Asn
            100                 105                 110

Asn Trp Ser Asp Tyr Gly Gly Ile Asn Ala Tyr Val Asn Ala Phe Gly
            115                 120                 125

Gly Asn Ala Thr Thr Trp Tyr Thr Asn Thr Ala Ala Gln Thr Gln Tyr
        130                 135                 140

Arg Lys Tyr Val Gln Ala Val Val Ser Arg Tyr Ala Asn Ser Thr Ala
145                 150                 155                 160

Ile Phe Ala Trp Glu Leu Gly Asn Glu Pro Arg Cys Asn Gly Cys Ser
                165                 170                 175

Thr Asp Val Ile His Gln Trp Ala Thr Ser Val Ser Gln Tyr Val Lys
            180                 185                 190

Ser Leu Asp Ser Asn His Leu Val Ser Leu Gly Asp Glu Gly Phe Gly
```

```
              195                 200                 205
Leu Ser Thr Gly Asp Gly Thr Tyr Pro Tyr Tyr Gly Glu Gly Thr
        210                 215                 220

Asp Phe Ala Lys Asn Val Gln Ile Lys Ser Leu Asp Phe Gly Thr Phe
225                 230                 235                 240

His Leu Tyr Pro Asp Ser Trp Gly Thr Asn Tyr Thr Trp Gly Asn Gly
                245                 250                 255

Trp Ile Arg Thr His Ala Ala Ala Cys Leu Ala Ala Gly Lys Pro Cys
                260                 265                 270

Val Leu Glu Glu Tyr Gly Ala Gln Gln Asn Pro Cys Thr Asn Glu Ala
            275                 280                 285

Pro Trp Gln Thr Thr Ser Leu Thr Thr Arg Gly Met Gly Gly Asp Met
        290                 295                 300

Phe Trp Gln Trp Gly Asp Thr Phe Ala Asn Gly Ala Gln Ser Asn Ser
305                 310                 315                 320

Asp Pro Tyr Thr Val Trp Tyr Asn Ser Ser Asn Trp Gln Cys Leu Val
                325                 330                 335

Lys Asn His Val Asp Ala Ile Asn Gly Gly Thr Thr Thr Pro Pro Pro
                340                 345                 350

His His His His His
        355

<210> SEQ ID NO 10
<211> LENGTH: 58
<212> TYPE: PRT
<213> ORGANISM: Artificial Sequence
<220> FEATURE:
<223> OTHER INFORMATION: CBD region aa

<400> SEQUENCE: 10

Val Ser Ser Thr Thr Thr Thr Ser Ser Arg Thr Ser Ser Thr Pro Pro
1               5                   10                  15

Pro Pro Gly Gly Ser Cys Ser Pro Leu Tyr Gly Gln Cys Gly Gly Ser
            20                  25                  30

Gly Tyr Thr Gly Pro Thr Cys Cys Ala Gln Gly Thr Cys Ile Tyr Ser
        35                  40                  45

Asn Tyr Trp Tyr Ser Gln Cys Leu Asn Thr
50                  55
```

US 9,040,277 B2

MANNANASE VARIANTS

RELATED APPLICATIONS

This application is a national stage application (under 35 U.S.C. §371) of PCT/EP2010/007123, filed Nov. 24, 2010, which claims benefit of U.S. Provisional Application 61/294,684, filed Jan. 13, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_01427_US. The size of the text file is 28 KB and the text file was created on Jul. 13, 2012.

FIELD OF THE DISCLOSURE

The technology provided herein relates to improved variants of microbial mannanases more specifically to microbial enzymes exhibiting mannanase activity as their major enzymatic activity; to nucleic acid molecules encoding said mannanases, vectors, host cells containing the nucleic acids and methods for producing the mannanases; compositions comprising said mannanases; methods for preparation and producing such enzymes; and to methods for using such enzymes for food and feed processing, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, as baking ingredients, for removal of biofilms and in delivery systems, for grain processing or for the processing of renewable resources intended for the production of biological fuels, and in the textile, oil drilling, cleaning, laundering, detergent, and cellulose fiber processing industries.

BACKGROUND

Endo-β-1,4-D-mannanase (β-mannanase; EC 3.2.1.78) catalyses the random hydrolysis of manno-glycosidic bonds in mannan-based polysaccharides. Most β-mannanases degrade oligosaccharides down to DP4 (Biely and Tenkanen (1998) *Enzymology of hemicellulose degradation*, pages 25-47. In Harman and Kubiceck (ed) *Trichoderma and Gliocladium*, vol. 2, Taylor and Francis Ltd. London), however, residual activity has been demonstrated on mannotriose, indicating at least four subsites for mannose binding on the protein. The main end products of hydrolysis are often mannobiose and mannotriose, although significant amounts of mannose are also produced. Some β-mannanases are able to degrade crystalline mannan. In addition to hydrolysis, several β-mannanases including β-mannanase from *Trichoderma reesei*, have been shown to form transglycosylation products with either mannose or mannobiose as glycosidic bond acceptor.

β-mannanases have been isolated from a wide range of organisms including bacteria, fungi, plants and animals. Although mostly extracellular, some β-mannanases appear to be cell-associated. Their expression is often induced by growth on mannan or galactomannan, however, β-mannanase from *T. reesei* can also be induced by cellulose, while its expression is suppressed by glucose and other monosaccharides. Frequently multiple mannanases with different isoelectric points are found in the same organism, representing products from different genes or different products from the same gene, respectively.

In general, β-mannanases have moderate temperature optima between 40° C. and 70° C., except some β-mannanases from thermophiles (Politz et al. (2000) A highly thermostable endo-1,4-β-mannanase from the marine bacterium *Rhodothermus marinus; Appl. Microbiol. Biotechnol.* 53:715-721). The pH-optimum is in the neutral or acidic region, e.g. pH 5.0 for β-mannanase from *T. reesei* (Arisan-Atac et al. (1993) Purification and characterisation of a β-mannanase of *Trichoderma reesei* C-30; *Appl. Microbiol. Biotechnol.* 39:58-62). The molecular weights of the enzymes range between 30 kD and 80 kD.

WO 002008009673 discloses variants of *Trichoderma reesei* mannanases improved in thermal stability and low pH/pepsin resistance for the use in hydrolysis of galactomannan containing plant material, e.g. palm kernel expeller (PKE) and for the use in animal feed. For example, thermostability is required for feed additives that are incorporated in the feed mixtures prior to a pelleting procedure that comprises high temperatures. Additionally, mannanases applicable as feed additives need to be low-pH- and pepsin-stable and have to be active at low pH in order to be able to work efficiently in the stomach of e.g. monogastric animals.

However, the trend in the feed industry is to increase the pelleting temperatures further and further. Currently enzyme stability around 90° C. to 95° C. pelleting temperature is targeted to enable the use of enzymes throughout all industrially relevant feed production plants. Therefore the availability of a mannanase with improved thermal stability would be highly advantageous, as it would allow using the enzyme also in plants with high operation temperature.

SUMMARY OF THE DISCLOSURE

In a first aspect, embodiments of the disclosure provide mannanase variants which have an amino acid sequence that varies from that of the parent/wild type *Trichoderma reesei* mannanase (SEQ ID NO: 1), and which have one or more advantageous properties. Such properties may include but are not limited to favourable: thermo stability; temperature/activity profile; pH/activity profile; specific activity; and pH/protease-sensitivity.

In a further aspect, embodiments of this disclosure relate to a mannanase variant comprising a mannanase that contains a substitution at one or more positions selected from the group consisting of: 66, 215 or 259, wherein each position corresponds to the position of the amino acid sequence of the parent/wild type *Trichoderma reesei* mannanase (SEQ ID NO: 1).

In a further aspect, embodiments of this disclosure relate to mannanase variants which have an amino acid sequence that varies from that of the parent/wild type *Trichoderma reesei* mannanase (SEQ ID NO: 1), comprising the variation 201S, 207F and 274L, and at least a variation at one or more positions corresponding to position 66, 215 or 259 as compared to the amino acid sequence of SEQ. ID NO: 1.

In still another aspect, embodiments of this disclosure provide nucleic acids encoding mannanase variants as disclosed herein, as well as vectors and host cells comprising such nucleic acids. In yet other embodiments, the sequences are employed in processes that yield the mannanase variants.

Further, embodiments of this disclosure relate generally to the use of the mannanase variants for digestion of galactomannan, in particular catalyses the random hydrolysis of manno-glycosidic bonds in mannan-based polysaccharides.

Advantageously, mannanase variants of this disclosure may be used in industrial applications including, for example, methods for starch liquefaction and for enhancing digestion of galactomannan in foods and animal feeds. Advantageously, mannanase variants according to embodiments of the present disclosure are useful and used in alcohol fermentations processes and/or productions, for coffee extraction and the processing of coffee waste, as a supplement to food and feed, for enzyme aided bleaching of paper pulps, as bleaching and/or desizing agent in textile industry, for oil and gas well stimulation by hydraulic fracturing, as detergent, as baking ingredients, for removal of biofilms and in delivery systems, for grain processing or for the processing of renewable resources intended for the production of biological fuels, and in the textile, oil drilling, cleaning, laundering, detergent, and cellulose fiber processing industries.

In other aspects, this disclosure relates to enzyme compositions comprising a mannanase variant as described herein, wherein the enzyme composition is useful for, or used in, commercial applications. In one embodiment, the enzyme composition may be an animal feed composition. In other embodiments, the enzyme composition may be used in starch hydrolysis (e.g. liquefaction) processes. In an advantageous embodiment, the variants and/or the enzyme composition may be used in alcohol fermentation processes. In further embodiments, an enzyme composition comprising a mannanase encompassed by this disclosure will include additional enzymes, such as phytases, glucoamylases, alpha amylases, protease, cellulases, hemicellulases and combinations thereof.

In a further aspect, embodiments of this disclosure relate to methods for producing the mannanase variants in a host cell by transforming the host cell with a DNA construct, advantageously including a promoter having transcriptional activity in the host cell, cultivating the transformed host cell in a suitable culture medium to allow expression of said mannanase and producing the mannanase. The method may also include recovering the produced mannanase. In one embodiment, the host cell is a fungi like *Trichoderma*, such as *T. reesei*, a yeast, a bacterial or a plant cell. In an advantageous embodiment of this disclosure, the mannanase variant has the sequence of SEQ ID NO: 4, SEQ ID NO: 6, SEQ ID NO: 7, SEQ ID NO: 8 or SEQ ID NO: 9 or variants, modified forms, homologs, fusion proteins, functional equivalents or fragments thereof.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications referenced above, in particular the disclosure of WO 2008/009673.

BRIEF DESCRIPTION OF THE DRAWINGS

FIG. 1 shows an amino acid sequence of a wild-type *Trichoderma reesei* mannanase, (SEQ ID NO: 1).

FIG. 2 shows the amino acid sequence of a *Trichoderma reesei* mannanase variant V-31 disclosed in WO 2008/009673 (SEQ ID NO: 2).

FIG. 3 shows the amino acid sequence of a further *Trichoderma reesei* mannanase variant V-31/S3R disclosed in WO 2008/009673 (SEQ ID NO: 3).

FIG. 4 shows the amino acid sequence of an advantageous mannanase variant TM-1 according to the present disclosure (SEQ ID NO: 4).

FIG. 5 shows the nucleic sequence of the mannanase variant TM-1 (SEQ ID NO: 4) according to the present disclosure (SEQ ID NO: 5).

FIG. 6 shows the amino acid sequence of a further advantageous mannanase TM-100 variant according to the present disclosure (SEQ ID NO: 6).

FIG. 7 shows the amino acid sequence of a further advantageous mannanase variant TM-108 according to the present disclosure (SEQ ID NO: 7).

FIG. 8 shows the amino acid sequence of a further advantageous mannanase variant TM-CBD-148 according to the present disclosure (SEQ ID NO: 8).

FIG. 9 shows the amino acid sequence of a further advantageous mannanase variant TM-144 according to the present disclosure (SEQ ID NO: 9).

FIG. 11 shows the amino acid sequence of a Cellulose Binding Domain (CBD).

DETAILED DESCRIPTION OF THIS DISCLOSURE

Figure 10:
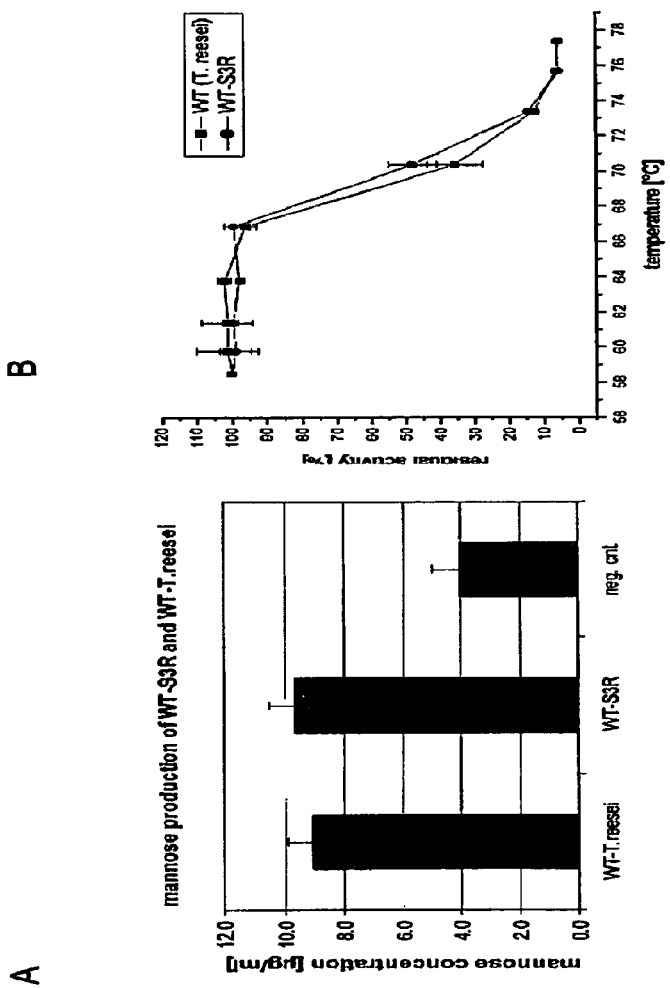
FIG. 10 shows the comparison of the parent/wild type *Trichoderma reesei* mannanase and the S3R-variant with respect to thermal stability and activity.

Disclosed herein are variants of *Trichoderma reesei* mannanases (EC 3.2.1.78) and nucleic acid encoding the mannanases that may be used in industrial applications including methods for protein hydrolysis, biomass degradation and for enhancing digestion of galactomannan contained in food and/or animal feed.

In particular, mannanase variants according to the present disclosure showing particular improved thermal stability, pH/pepsin stability and at the same time improved or retained specific activities compared to the parent mannanase enzyme used. These characteristics make them specifically useful for an industrial application in animal feeds, food and for galactomannan degradation in plant material in general.

The present disclosure reveals enzymes with an amino-acid sequence derived from the amino acid sequence shown in SEQ ID NO:1 or variants, modified forms, homologs, fusion proteins, functional equivalents or fragments thereof, or comprising one or more insertions, deletions or mutations or any combination thereof. A homologous mannanase according to the present disclosure comprises any enzyme with a sequence identity of at least 70% or preferably at least 80%, 85%, 90%, 95%, 97% or 99%, preferably to SEQ ID NO:1, more preferably to SEQ ID NO: 4, SEQ ID NO: 6, SEQ ID NO: 7, SEQ ID NO: 8 or SEQ ID NO: 9.

The mannanase variants of this disclosure have mannanase activity and an amino acid sequence that varies from the amino acid sequence of the parent/wild type *Trichoderma reesei* mannanase (SEQ ID NO: 1) in comprising one or more variations (including substitutions, insertions and deletions).

In an advantageous embodiment, the amino acid sequence of the mannanase variants comprises at least the variation 201S, 207F and 274L, and at least a variation at one or more positions corresponding to position 66, 215 or 259 as compared to the amino acid sequence of SEQ. ID NO: 1. For example, advantageously the variation in the mannanase variants can be selected from the group consisting of: 66P, 215T and 259R.

An advantageous embodiment of the disclosure is a mannanase variant according to SEQ ID NO: 4 or variants, modified forms, homologs, fusion proteins, functional equivalents or fragments thereof, or comprising one or more insertions, deletions or mutations or any combination thereof, and a mannanase which has at least a minimum percentage sequence identity and/or percent homology to the mannanase of SEQ ID NO: 4, wherein the minimum percent identity and/or homology is at least 50%, at least 60%, at least 75%, at least 80%, at least 85%, at least 90%, at least 93%, at least 96%, at least 97%, at least 98% or at least 99%.

In further advantageous embodiments, mannanase variants according to the present disclosure comprise in additional to the variations 201S, 207F and 274L and to a variation at one or more positions corresponding to position 66, 215 or 259 a variation at position 3 and/or 181 corresponding to the position of the amino acid sequence of SEQ ID NO: 1. For example, the variation at position 3 is 3R, the variation at position 181 is 181A or 181H (181/A/H).

In further advantageous embodiments, the mannanase variants according to the present disclosure comprises the variations 201S, 207F and 274L and at least variations at position 66, 215, and 259 as compared to the amino acid sequence of SEQ. ID NO: 1. In an advantageous example the variations at positions 66, 215 and 259 respectively are 66P, 215T and 259R.

In a further embodiment, the mannanase variants comprise in addition to the variations 201S, 207F and 274L and at position 66, 215, and 259 a variation in position, preferably 181A/H as compared to the amino acid sequence of SEQ. ID NO: 1. In an advantageous embodiment, the mannanase variants comprise further a variation in position 3, like 3R.

In an advantageous embodiment, the amino acid sequence of the mannanase variants according to the present disclosure comprises at least the variation 201S, 207F and 274L, and at least a variation at one or more positions corresponding to position 66, 215 or 259 and one or more additional variations, wherein the variation position is 31, 97, 113, 146, 149, 173, 181, 280, 282, 331 or 344 as compared to the amino acid sequence of SEQ. ID NO: 1. For example, the variations are 31Y, 97R, 113Y, 146Q, 149K, 173H/T, 181H/A, 280S/L/R, 282D, 331S or 344D.

Advantageous embodiments of the disclosure are mannanase variants which have at least a minimum percentage sequence identity and/or percent homology to the mannanases according to the present disclosure, wherein the minimum percent identity and/or homology is at least 50%, at least 60%, at least 75%, at least 80%, at least 85%, at least 90%, at least 93%, at least 96%, at least 97%, at least 98% or at least 99%.

Advantageous embodiments are further mannanase variants having mannanase activity and an amino acid sequence that varies from the amino acid sequence of parent/wild type *Trichoderma reesei* mannanase (SEQ ID NO:1), wherein the amino acid of the mannanase variant comprises the variations 201S, 207F and 274L, and at least variations selected from the group consisting of:

1) F31Y/S66P/Q97R/N113Y/N173H/V181H/A215T/Q259R/Q280R/N282D/N331S
2) S66P/Q97R/N113Y/N173H/V181A/A215T/Q259R/Q280S/N331S
3) F31Y/S66P/Q97R/N173H/V181H/A215T/Q259R/Q280R/N282D
4) F31Y/S66P/Q97R/N173H/V181H/A215T/Q259R/Q280S/N282D/N331S
5) F31Y/S66P/Q97R/N113Y/N173H/V181H/A215T/Q259R/Q280R/N282D
6) F31Y/S66P/Q97R/Q149K/N173H/V181H/A215T/Q259R/Q280L
7) S66P/Q97R/N113Y/N173H/V181A/A215T/Q259R
8) F31Y/S66P/Q97R/N113Y/N173H/V181H/A215T/Q259R/Q280S/N282D/N331S
9) S66P/N113Y/N173H/V181H/A215T/Q259R
10) F31Y/S66P/Q97R/N113Y/K146Q/N173H/V181H/A215T/Q259R/Q280L/N282D
11) F31Y/S66P/Q97R/N113Y/K146Q/N173H/V181A/A215T/Q259R/Q280L/N282D/N331S
12) F31Y/S66P/Q97R/N113Y/K146Q/N173H/V181H/A215T/Q259R/Q280L
13) F31Y/S66P/Q97R/N173H/V181H/A215T/Q259R/N282D
14) F31Y/S66P/Q97R/N113Y/K146Q/N173H/V181A/A215T/Q259R/Q280R/N282D
15) S66P/N113Y/V181H/A215T/Q259R
16) S66P/Q97R/N113Y/N173H/V181H/A215T/Q259R/Q280L/N282D
17) F31Y/S66P/Q97R/N113Y/K146Q/N173H/V181A/A215T/Q259R/Q280L/N282D
18) F31Y/S66P/N173H/V181H/A215T/Q259R/N282D
19) F31Y/S66P/Q97R/N173H/V181H/A215T/Q259R/Q280L
20) S66P/Q97R/N113Y/N173H/V181H/A215T/Q259R/Q280R/N282D
21) F31Y/S66P/Q97R/N113Y/N173T/V181H/A215T/Q259R/Q280R/N282D
22) F31Y/S66P/Q97R/N173T/V181H/A215T/Q259R/Q280R/N282D
23) F31Y/S66P/Q97R/N173H/V181H/A215T/Q259R/Q280S/N282D
24) S66P/N113Y/N173H/V181H/A215T/Q259R/Q280S/N282D
25) S66P/Q97R/N113Y/N173H/V181A/A215T/Q259R/Q280S/N282D/N331S
26) S66P/Q97R/N113Y/V181H/A215T/Q259R/Q280L/N282D
27) S66P/N113Y/N173H/V181H/A215T/Q259R/N331S
28) F31Y/S66P/Q97R/N113Y/K146Q/N173H/V181A/A215T/Q259R/Q280R/N282D/N331S
29) F31Y/S66P/Q97R/N113Y/K146Q/V181H/A215T/Q259R/Q280S/N282D/N331S
30) S66P/Q97R/N113Y/N173T/V181A/A215T/Q259R
31) F31Y/S66P/Q97R/N113Y/K146Q/N173H/V181A/A215T/Q259R/Q280S/N331S
32) F31Y/S66P/Q97R/N113Y/V181H/A215T/Q259R
33) S66P/Q97R/N113Y/N173H/V181A/A215T/Q259R/N331S
34) F31Y/S66P/Q97R/N113Y/V181H/A215T/Q259R/Q280L
35) F31Y/S66P/Q97R/N113Y/K146Q/V181H/A215T/Q259R/Q280L
36) F31Y/S66P/Q97R/K146Q/V181H/A215T/Q259R/Q280R/N282D
37) S66P/N113Y/V181H/A215T/Q259R/N282D
38) F31Y/S66P/Q97R/V181H/A215T/Q259R/N282D
39) S66P/N113Y/N173H/V181H/A215T/Q259R/Q280S/N331S
40) F31Y/S66P/Q97R/N113Y/K146Q/N173H/V181H/A215T/Q259R/Q280S/N331S
41) S66P/V181H/A215T/Q259R/N282D

42) F31Y/S66P/Q97R/N113Y/K146Q/V181H/A215T/Q259R/Q280L/N331S
43) S66P/Q97R/N113Y/N173H/V181H/A215T/Q259R/N282D
44) S66P/Q97R/N113Y/V181H/A215T/Q259R/N282D
45) S66P/V181H/A215T/Q259R
46) S66P/Q97R/N113Y/V181H/A215T/Q259R/Q280R/N282D
47) F31Y/S66P/N173T/V181H/A215T/Q259R/N282D
48) F31Y/S66P/N113Y/V181H/A215T/Q259R/Q280R/N344D
49) F31Y/S66P/Q97R/N113Y/N173H/V181H/A215T/Q259R/Q280R/N282D
50) F31Y/S66P/Q97R/N113Y/N173H/V181H/A215T/Q259R/Q280S/N282D/N331S
51) S66P/N113Y/N173H/V181H/A215T/Q259R/Q280S
52) S66P/Q97R/N113Y/N173H/V181A/A215T/Q259R
53) S66P/Q97R/N113Y/N173H/V181A/A215T/Q259R/Q280S
54) S66P/N113Y/N173H/V181H/A215T/Q259R/Q280S/N282D
55) F31Y/S66P/Q97R/N173H/V181H/A215T/Q259R/Q280R/N282D
56) S66P/N113Y/N173H/V181H/A215T/Q259R
57) S66P/Q97R/N113Y/N173H/V181A/A215T/Q259R/N331S
58) F31Y/S66P/Q97R/N173H/V181H/A215T/Q259R/Q280S/N282D/N331S
59) S66P/N113Y/N173H/V181H/A215T/Q259R/Q280S/N331S
60) S66P/Q97R/N113Y/N173H/V181A/A215T/Q259R/Q280S/N331S
61) F31Y/S66P/Q97R/Q149K/N173H/V181H/A215T/Q259R/Q280S/N331S
62) S66P/A215T/Q259R
63) S3R/S66P/A215T/Q259R

Embodiments of this disclosure also include variants of any of the mannanases set forth in sequences 1) to 63), which have mannanase activity and an amino acid sequence having a percent sequence identity and/or percent homology of at least 50%, at least 60%, at least 75%, at least 80%, at least 85%, at least 90%, at least 93%, at least 95%, at least 96%, at least 97%, at least 98%, and at least 99% as compared to each of the mannanase variants set forth in sequences 1) to 63).

Further embodiments of the disclosure are nucleic acid molecules, selected from the group consisting of
a) a nucleic acid molecule encoding the mannanase variants according to the present disclosure;
b) a nucleic acid molecule encoding for a derivative of the mannanase variants according to the present disclosure, preferably in which derivative one or more amino acid residues are conservatively substituted;
c) a nucleic acid molecule that is a fraction, variant, homologue, derivative, or fragment of the nucleic acid molecule presented as SEQ ID NO: 5;
d) a nucleic acid molecule that is capable of hybridizing to any of the nucleic acid molecules of a)-c) under stringent conditions
e) a nucleic acid molecule that is capable of hybridizing to the complement of any of the nucleic acid molecules of a)-c) under stringent conditions
f) a nucleic acid molecule having a sequence identity of at least 95% with any of the nucleic acid molecules of a)-e) and encoding for a mannanase,
g) a nucleic acid molecule having a sequence identity of at least 70% with any of the nucleic acid molecules of a)-e) and encoding for a mannanase,
h) or a complement of any of the nucleic acid molecules of a)-g).

Further embodiments of the disclosure are vectors and host cells comprising nucleic acid molecules encoding the mannanase variants according to the present disclosure.

Further, embodiments are methods for preparing the mannanase variants according to the disclosure, which comprises culturing the transformed host cell and isolating the modified mannanase from the culture.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

In one embodiment of the present disclosure, the mannanase enzymes show particularly improved thermal stability and at the same time improved or retained specific activities compared to the mannanase enzymes disclosed in WO 2008/009673. These characteristics make them specifically useful for an industrial application in animal feeds, food and for galactomannan degradation in plant material in general.

Therefore, the present disclosure is also directed to a method for the production of mannanases in *Trichoderma reesei*, active at low pH values as present in the stomach and upper intestine of animals and the crop, stomach and upper intestine of poultry. It is yet another object of the present disclosure to provide a manannase which can be added to animal feed prior to pelleting, in order to allow a precise and reproducible enzyme dosage, and avoid an additional spraying step in the feed preparation.

The term "mannanase" refers to any enzyme capable of hydrolyzing polyose chains that are composed of mannose units (mannopolymers or polymannoses). "Mannanase" therefore comprises both endomannanases and exomannanases which cleave mannopolymers internally or from the terminal ends of the polymer, respectively.

The term "functional equivalent of a mannanase" or "functional equivalent thereof" means that the enzyme has to have about the same functional characteristics as that of *Trichoderma reesei* mannanase.

The term "modified form" or "variant" means that the enzyme has been modified from its original form (parent/wild-type, wt) but retains the same enzymatic functional characteristics as that of *Trichoderma reesei* mannanase.

The term "fusion proteins" comprises all proteins derived from the parent mannanase or any variant thereof by covalently fusing additional amino-acid sequences at the C- and/or N-terminus. The source and composition of the additional amino-acid sequence is either natural from any living organisms or virus or unnatural.

The term "functional fragment" or "effective fragment" means a fragment or portion of the *Trichoderma reesei* mannanase or derivative thereof that retains about the same enzymatic function or effect.

The term "homologous mannanase" according to the present disclosure comprises any enzyme with a sequence identity of at least 70% or preferably at least 80%, 85%, 90%, 95%, 97% or 99% to the parent mannanase.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "position" in a polynucleotide or polypeptide refers to specific single bases or amino acids in the sequence of the polynucleotide or polypeptide, respectively.

The term "polypeptide" comprises proteins such as enzymes, antibodies and the like, medium-length polypeptides such as peptide inhibitors, cytokines and the like, as well as short peptides down to an amino acid sequence length below ten, such as peptidic receptor ligands, peptide hormones, and the like.

The term "mannanase variants" means any mannanase molecule obtained by site-directed or random mutagenesis, insertion, deletion, recombination and/or any other protein engineering method, which leads to mannanases that differ in their amino acid sequence from the parent mannanase. The terms "wild type mannanase", "wild type enzyme", or "wild type" in accordance with the disclosure describe a mannanase enzyme with an amino acid sequence found in nature or a fragment thereof.

The "parent mannanase" can be either an isolated wild-type mannanase or a fragment thereof, or one or more mannanase variants selected from a library of mannanases. The term "mannanase library" describes at least one mannanase variant or a mixture of mannanases in which every single mannanase, resp. every mannanase variant, is encoded by a different polynucleotide sequence.

The term "gene library" indicates a library of polynucleotides that encodes the library of mannanases.

The term "isolated" describes any molecule separated from its natural source.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 1 either in one- or in three-letter code.

The term "nucleic acid molecule" or "nucleic acid" is intended to indicate any single- or double stranded nucleic acid molecule of cDNA, genomic DNA, synthetic DNA or RNA, PNAS or LNA origin The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "fragment of the nucleic acid molecule" is intended to indicate a nucleic acid comprising a subset of a nucleic acid molecule according to one of the claimed sequences. The same is applicable to the term "fraction of the nucleic acid molecule".

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "derivative," as used herein, refers to a nucleic acid molecule that has similar binding characteristics to a target nucleic acid sequence as a nucleic acid molecule according to one of the claimed sequences

TABLE 1

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Mutations or variations are described by use of the following nomenclature: position; substituted amino acid residue(s). According to this nomenclature, the substitution of, for instance, an alanine residue for a glycine residue at position 20 is indicated as 20G. When an amino acid residue at a given position is substituted with two or more alternative amino acid residues these residues are separated by a comma or a slash. For example, substitution of alanine at position 30 with either glycine or glutamic acid is indicated as 20G/E, or 20G, 20E.

Furthermore, the following nomenclature could also be used: amino acid residue in the protein scaffold; position; substituted amino acid residue(s). According to this nomenclature, the substitution of, for instance, an alanine residue for a glycine residue at position 20 is indicated as Ala20Gly or A20G, or 20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as Δ(Ala20-Gly21) or Δ(A20-G21). When a sequence contains a deletion in comparison to the parent protein used for numbering, an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

TABLE 2

Venn diagram grouping amino acids

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The term "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. Therefore the residual activity $a_i$ is given by $a_i = v_i/v_0$ where v denotes any measure of catalytic activity and $a_i*100$ is the relative activity in percent. The term "specific activity" describes quantitatively the catalytic activity per amount of enzyme under defined reaction conditions.

The term "thermostability", "temperature stability" or "thermal stability" describes the property of a protein to withstand a limited heat exposure without losing its activity at lower temperatures, e.g. at the temperature where its activity can be measured.

The term "pH-stability" describes the property of a protein to withstand a limited exposure to pH-values significantly deviating from the pH where its stability is optimal, e.g. more than one pH-unit above or below the pH-optimum, without losing its activity under conditions where its activity can be measured.

The term "proteolytic stability" describes the property of a protein to withstand a limited exposure to proteases under conditions where the proteases are active, without loosing activity under conditions where its activity can be measured.

The term "plasmid", "vector system" or "expression vector" means a construct capable of in vivo or in vitro expression. In the context of the present disclosure, these constructs may be used to introduce genes encoding enzymes into host cells.

The term "host cell" in relation to the present disclosure includes any cell that comprises either the nucleic acid molecule or an expression vector as described above and which is used in the recombinant production of an enzyme having the specific properties as defined herein or in the methods of the present disclosure.

The "inactivation temperature" is defined as the temperature at which the residual activity of a mannanase enzyme after incubation for certain duration and subsequent cooling to room temperature is 50% of the residual activity of the same mannanase enzyme incubated for the same duration under the same conditions at room temperature.

The term "renewable resources" refers to biomass substrates which are grown and harvested, like crops, straw, wood and wood products. The term "biological fuels" refers to solid, liquid, or gas fuel consisting of, or derived from biomass, like Biodiesel, Biogas, Vegetable oil, Bioethanol, BioHydrogen, Bio-Dimethyl ether, Biomethanol, BTL ("Biomass to liquid")-Fuel, GTL ("Gas to liquid")-Fuel, and the like.

The term "functional equivalent thereof" means that the enzyme has to have about the same functional characteristics as that of Trichoderma reesei mannanase. The term "modified form" or "variant" means that the enzyme has been modified from its original form but retains the same enzymatic functional characteristics as that of Trichoderma reesei mannanase. In particular, the terms "variant" or "modified form" encompass mannanase enzymes with an amino acid sequence derived from the amino acid sequence of the parent/wild-type mannanase and having one or more amino acid substitutions, insertions, deletions or any combination thereof, which together are referred to as mutations.

"Fusion proteins" comprise all proteins derived from the parent mannanase or any variant thereof by covalently fusing an additional amino-acid sequence to the C- and/or N-terminus of the parent mannanase.

"Percent sequence identity", with respect to two amino acid or polnucleotide sequences, refers to the percentage of residues that are identical in the two sequences when the sequences are optimally aligned. Thus, 80% amino acid sequence if means that 80% of the amino acids in two optimally aligned polypeptide sequences are identical. Percent identity can be determined, for example, by a direct comparison of the sequence information between two molecules by aligning the sequences. counting the exact number of matches between the two aligned sequences, dividing by the length of the shorter sequence, and multiplying the result by 100. Readily available computer programs can be used to aid in the analysis, such as ALIGN, Dayhoff, M.O. in "Atlas of Protein Sequence and Structure", M.0. Dayhoff et., Suppl. 3:353-358, National Biomedical Research Foundation, Washington, DC, Which adapts the local homology algorithm of Smith and Waterman (1981) Advances in Appl. Math. 2:482-489 for peptide analysis. Programs for determining nucleotide sequence identity are available in the Wisconsin Sequence Analysis Package, Version 8 (available from Genetics Computer Group, Madison, WI) for example, the BESTFIT, PASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology information (ncbi.nlm,nih.gov/). Likewise, computer programs for determining percent homology are also readily available.

A "feed" and a "food," respectively, means any natural or artificial diet, meal or the like or components of such meals intended or suitable for being eaten, taken in, digested, by an animal and a human being, respectively.

A "food or feed additive" is a compound or a multi component composition intended for or suitable for being added to food or feed. It may, but is not required to, comprise one or more compounds such as vitamins, minerals or feed enhancing enzymes and suitable carriers and/or excipients, and it is usually provided in a form that is suitable for being added to animal feed. Modified forms or variants may display altered enzyme characteristics compared to the parent enzyme. Preferably, modified forms or variants have one or more of the following enhanced phenotypes: increased thermostability; and/or an increased proteolytic (for example against pepsin) stability; and/or an increased specific activity and/or improved stability at low pH. The term "functional" or "effective" fragment means a fragment or portion of the Trichoderma reesei mannanase that retains about the same enzymatic function or effect. It is also understood that the present disclosure comprises all molecules that are derived from the parent mannanase and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

Preferably, the said changes lead to improved properties of the enzyme such as
1. higher thermostability and/or
2. higher specific activity and/or
3. improved stability at low pH and/or
4. higher resistance against proteolytic cleavage by proteases such as pepsin; and/or
5. high residual activity at low pH.

In preferred embodiments of the present disclosure, the modified mannanase has a substitution at one or more of the positions 201, 207, 274, 66, 215, 259, 31, 97, 113, 146, 149, 173, 181, 280, 282, 331 or 344, relative to the numbering of parent/wild-type mannanase given in SEQ ID NO:1. These positions are characterized in that mutagenesis of the enzyme at these positions leads to improvement in the desired enzyme characteristics.

Yet basically, several amino-acid substitutions with respect to the parent/wild type mannanase have turned out beneficial in terms of thermo stability, both by themselves and/or in combination with others. These substitutions are shown in Table 3. Moreover, several amino acid substitutions have as well turned out to be quite beneficial in terms of pH stability, stability against proteases (particularly Pepsin) and/or specific activity. These substitutions are shown in Table 4.

In yet a further aspect, the disclosure relates to a nucleic acid molecule and to the use of a nucleic acid molecule selected from the group consisting of
(a) a nucleic acid molecule encoding a modified mannanase according to the above description,
(b) a nucleic acid molecule encoding for a derivative of the modified mannanase according to the above description, in which derivative one or more amino acid residues are conservatively substituted;
(c) the nucleic acid molecule presented as SEQ ID NO:5,
(d) a nucleic acid molecule that is a variant, homologue, derivative or fragment of the nucleic acid molecule presented as SEQ ID NO:5;
(e) a nucleic acid molecule that is the complement of the nucleic acid molecule set out in SEQ ID NO:5;
(f) a nucleic acid molecule that is the complement of a variant, homologue, derivative or fragment of the nucleic acid molecule presented as SEQ ID NO:5;
(g) a nucleic acid molecule that is capable of hybridizing to the nucleic acid molecule set out in SEQ ID NO:5;
(h) a nucleic acid molecule that is capable of hybridizing to a variant, homologue, derivative or fragment of the nucleic acid molecule presented as SEQ ID NO:5;
(i) a nucleic acid molecule that is the complement of a nucleic acid molecule that is capable of hybridizing to the nucleic acid molecule set out in SEQ ID NO:5;
(j) a nucleic acid molecule that is the complement of a nucleic acid molecule that is capable of hybridizing to a variant, homologue, derivative or fragment of the nucleic acid molecule presented as SEQ ID NO:5;

(k) a nucleic acid molecule that is capable of hybridizing to the complement of the nucleic acid molecule set out in SEQ ID NO:5;

(l) a nucleic acid molecule that is capable of hybridizing to the complement of a variant, homologue, derivative or fragment of the nucleic acid molecule presented as SEQ ID NO:5.

(m) a nucleic acid molecule having a sequence identity of at least 95% with any of the nucleic acid molecules of a)-1) and encoding for a mannanase, (n) a nucleic acid molecule having a sequence identity of at least 70% with any of the nucleic acid molecules of a)-b) and encoding for a mannanase, and/or (o) a fraction or a complement of any of the nucleic acid molecules of a)-n).

A nucleotide or nucleic acid is considered to hybridize to one of the above nucleotides if it is capable of hybridizing under conditions of medium stringency, more preferably high stringency, even more preferably under very high stringency conditions.

To prepare a hybridization blot, standard molecular biology protocols for blotting may be used (e.g. Southern blotting for DNA hybridizations). The amount of target DNA depends on the relative abundance of the target sequence. If a pure target sequence is to be used, between 1 and 5 picograms of DNA per kilobase of polynucleotides are preferred. Typically, the detection limit is about 0.5 pg DNA for a radioactive probe with specific activity of $10^9$ dpm/mg which is equivalent to a single-copy gene 500 bp in length in 3.3 mg genomic DNA of a complex genome (e.g. human). In practice one will use approx. 10 mg of genomic DNA—for example to screen for organisms, such as micro-organisms, which contain a mannanase encoding polynucleotide of the disclosure. If the target DNA is bacterial or a plasmid one will have to dilute the DNA accordingly to avoid overexposure. The target DNA is blotted, e.g. by dot blotting, or via blotting from an electrophoresis gel. Preferred conditions are described in 'Membrane Transfer and Detection Methods, Amersham International plc, UK.-PI/162/85/1) Hybond N+ positively charged nylon membrane is preferably used (Amersham Life Science). The probe is preferably prepared according to Pharmacia's 'Ready to Go DNA™ labeling kit' to prepare a probe of >1×$10^9$ dpm/microgram. The probe is used in hybridization buffer at a concentration of 1×$10^6$ dpm per milliliter hybridization buffer. Blots are preferably prehybridized in hybridization buffer (6×SSC, 5×Reinhardt's solution, and 0.5% SDS, and denatured salmon sperm DNA to 100 mg/ml buffer) for an hour at 65° C., followed by hybridization in hybridization buffer containing the denatured labelled probe with shaking for 12 hours at 65° C. The blot(s) are then washed with a suitable volume wash buffer (typically 50 ml) in 2×SSC, 0.1% SDS for 30 minutes at 65° C., followed by a second wash in a suitable volume wash buffer (typically 50 ml) in either the same wash buffer (2×SSC, 0.1% SDS) for medium stringency washing, or 0.1%×SSC, 0.1% SDS for 10 minutes at 65° C. (high stringency), the second wash can be repeated at 70° C. for very high stringency washing. The nucleic acid molecule of the present disclosure may comprise nucleotide sequences that encode for SEQ ID NO:1 or an effective fragment thereof or a variant, modified form, homologue or derivative thereof.

In particular, the disclosure provides a plasmid or vector system comprising a nucleic acid sequence encoding a mannanase as described herein or a homologue or derivative thereof. Preferably, the plasmid or vector system comprises a nucleic acid coding for the amino acid SEQ ID NO:4 or a sequence that is at least 75% homologous thereto or an effective fragment thereof, or any of the derivatives of SEQ ID NO:1 described herein. Suitably the plasmid or vector system is an expression vector for the expression of any of the enzymes encoded by a nucleic acid sequence as set out in any of SEQ ID NO:4 or a sequence that is at least 75% homologous (identical) thereto in a microorganism. Suitable expression vectors are described herein. In addition, the disclosure provides a plasmid or vector system for expression of any of the modified enzymes or variants or functional fragments described herein. Suitable expression vectors are described herein.

Improvements in mannanase characteristics according to the present disclosure are directed to the use in a variety of technical processes such as but not limited to, the use as an additive to food and feed products, for food and feed processing, pulp and paper production, as well as for oil/gas well stimulation by hydraulic fractioning, generation of slow release formulations of drugs or in detergents, in particular in the removal of bacterial biofilms. In particular, improvements are directed to the enzyme stability under conditions of these or other applications and/or to the stability during stomach transit in case of a food or feed additive and/or to the activity or stability in human or animal stomach and/or intestinal tract under the acidic conditions of the upper gastrointestinal tract. Such improvements comprise, among other parameters, the increase in stability at elevated temperatures, preferably at temperatures above 60° C. and/or the increase in stability against proteolytic digestion, preferably against proteases of the digestive tract and/or the increase in stability at low pH and/or the activity at low pH values and/or the general efficiency of releasing mannose and/or oligomannoses from large polymannose containing carbohydrates.

The increase in stability at elevated temperatures is quantified by the inactivation temperature of the enzyme. The inactivation temperature is defined as the temperature at which the residual activity of a mannanase enzyme after incubation for certain duration and subsequent cooling to room temperature is 50% of the residual activity of the same mannanase enzyme incubated for the same duration under the same conditions at room temperature.

Thermostability differences are the differences in ° C. between the inactivation temperatures of two enzymes. In a preferred embodiment of the disclosure the mannanase variants are applied in processes at elevated temperatures, making mannanase variants with a higher inactivation temperature desirable.

When compared with wild-type mannanase, mannanases of the disclosure are characterised by a higher residual activity after a thermal incubation at temperatures above the inactivation temperature of the wild-type mannanase, providing higher process stability.

Cloning of *T. reesei* mannanase: In addition to the *Trichoderma reesei* mannanase as shown in SEQ ID NO:1 a further *Trichoderma reesei* mannanase has been cloned having the sequence of SEQ ID NO:1 with a substitution of serine to arginine at position 3 (mutation S3R). This mannanase variant was compared to the *Trichoderma reesei* mannanase according to SEQ ID NO:1 with respect to thermal stability and catalytic activity in releasing mannose from a polymannose containing substrate. The results presented in FIG. 10 demonstrate that the S3R substitution has no effect on the properties relevant to the disclosure and is therefore a neutral mutation (see also WO 2008/009673). Therefore, in the context of this disclosure the term "wt" or "wt mannanase" "wild-type mannanase" or "*Trichoderma reesei* mannanase" is understood to comprise the mannanases according to SEQ ID NO:1 and the mannanase according to SEQ ID NO: 1 having in addition the neutral mutation S3R.

Thermostability in Buffer: In a preferred embodiment of the disclosure, mannanase variants have an increased residual activity and/or inactivation temperature when incubated at temperatures >60° C. for >30 min. In a more preferred embodiment the increased residual activity and/or inactivation temperature is obtained after incubation in an acetate buffer for 45 min. Preferably, the inactivation temperature of the mannanase variant is >68° C., more preferably >70° C. or >72° C. or >74° C., or most preferably >84° C. Specific inactivation temperatures are given in table 3 in conjunction with their respective mutations.

Fusion Proteins: It is also understood that the amino acid sequence revealed in SEQ ID NO:1 and derivatives thereof described herein for the use according to the present disclosure may be produced as a N- and/or C-terminal fusion protein, for example to aid in extraction, detection and/or purification and/or to add functional properties to the mannanase molecule. The fusion protein partner may be any protein or peptide including any polypeptide sequence derived from the native host, any other naturally occurring amino-acid sequence as well as synthetic sequences. Examples of fusion protein partners include, but are not limited to, glutathione-S-transferase (GST), 6×His, GAL4 (DNA binding and/or transcriptional activation domains), FLAG-, MYC-tags or other tags well known to anyone skilled in the art. It may also be convenient to include a proteolytic cleavage site between the fusion protein partner and the protein sequence of interest to allow removal of fusion protein sequences. Preferably, the fusion protein will not hinder the activity of the protein sequence of interest.

In a preferred embodiment of the disclosure the mannanase variants are fused to functional domains including leader peptides, propeptides, binding domains or catalytic domains.

Binding domains may include, but are not limited to, carbohydrate-binding domains of various specificities, providing increased affinity to carbohydrate components present during the application of the mannanase. It is also envisioned that the fusion partner domain may comprise enzymatically active domains, such as activities supporting the action of the mannanase in producing the desired product by providing activity on one or more components of the substrate and/or any product of the mannanase catalytic reaction. Non-limiting examples of catalytic domains include: cellulases, hemicellulases such as xylanase, exo-mannanases, glucanases, arabinases, galactosidases, pectinases, and/or other activities such as proteases, lipases, acid phosphatases and/or others or functional fragments thereof.

Linkers: Fusion proteins may optionally be linked to the mannanase through a linker sequence comprised of preferably less than 100 amino acids, more preferably less than 50 amino acids, less than 30 amino acids or less than 20 amino acids. The linker may simply join the mannanase and the fusion domain without significantly affecting the properties of either component, or it may optionally have functional importance for the intended application due to its amino acid composition, structure and/or posttranslational modification occurring during expression in the native host or any suitable heterologous host. The source of the linker sequence may be from an amino acid sequence from any organism or any synthetic peptide sequence.

Additional Proteins: The mannanases described herein for use according to the present description may also be used in conjunction with one or more additional proteins of interest (POIs) or nucleotide sequences of interest (NOIs). Non-limiting examples of POIs include: phytases, hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or others. These include enzymes that, for example, modulate the viscosity of the substrate solution/suspension or increase the accessibility and/or solubility of the polymannose substrate. The NOI may even be an antisense sequence for any of those sequences. As described above, the POI may even be a fusion protein. The POI may even be fused to a secretion sequence. In an advantageous embodiment, the mannanase variant according to the present disclosure is used in conjunction with at least a phytases.

Other sequences can also facilitate secretion or increase the yield of secreted POI. Such sequences could code for chaperone proteins as for example the product of *Aspergillus niger* cyp B gene described in UK patent application 9821198.0.

The NOI coding for POI may be engineered in order to alter their activity for a number of reasons, including but not limited to, alterations which modify the processing and/or expression of the expression product thereof. By way of further example, the NOI may also be modified to optimise expression in a particular host cell. Other sequence changes may be desired in order to introduce restriction enzyme recognition sites.

The NOI coding for the POI may include within it synthetic or modified nucleotides—such as methylphosphonate and phosphorothioate backbones.

The NOI coding for the POI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiester linkages within the backbone of the molecule.

Expression of Mannanase Genes: In order to produce a mannanase enzyme, the DNA encoding the enzyme can be chemically synthesized from published sequences or obtained directly from host cells harbouring the gene (e.g., by cDNA library screening or PCR amplification). The mannanase gene can be included in an expression cassette and/or cloned into a suitable expression vector by standard molecular cloning techniques. Such expression cassettes or vectors often contain sequences that assist initiation and termination of transcription (e.g., promoters and terminators), and may contain selectable markers. Cassettes can also be comprised of plus or minus strand mRNA, and their expression may or may not include an amplification step before translation of the mRNA. The mannanase gene to be expressed can contain or not contain certain domains of the protein, such as polymer binding domains (e.g., carbohydrate binding domains) of various specificities. The expression cassette or vector can be introduced in a suitable expression host cell which will then express the corresponding mannanase gene. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces, Staphylococcus* (e.g., *S. carnosus*), *Lactococcus* (e.g., *L. lactis*), lactic acid bacteria or *Bacillus* (*subtilis, megaterium, licheniformis,* etc.). Also particularly suitable are yeast expression hosts such as *Saccharomyces cerevisiae, Schizosaccharomyces pombe, Yarrowia lipolytica, Hansenula polymorpha, Kluyveromyces lactis* or *Pichia pastoris*. Especially suited are fungal expression hosts such as

*Aspergillus niger, Chrysosporium lucknowense, Aspergillus* (e.g., *A. oryzae, A. niger, A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines, transgenic mammalian systems such as rabbit, goat or cattle, other eukaryotic hosts such as insect cells or viral expression systems such as bacteriophages like M13, T7 phage or Lambda, or viruses such as Baculovirus expression systems, or plants.

Mannanase genes are introduced into expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the enzyme variants are expressed intracellularly. Optionally, after intracellular expression of the enzyme variants, or secretion into the periplasmic space using signal sequences such as those mentioned above, a permeabilisation or lysis step can be used to release the mannanase enzyme into the supernatant. The disruption of the membrane barrier can be effected by the use of mechanical means such as ultrasonic waves, pressure treatment (French press), cavitation or the use of membrane-digesting enzymes such as lysozyme or enzyme mixtures. As a further alternative, the genes encoding the mannanase enzyme are expressed cell-free by the use of a suitable cell-free expression system. For example, the S30 extract from *Escherichia coli* cells was used for this purpose or commercially available systems (e.g., CECF technology by Roche Applied Science, Inc.). In cell-free systems, the gene of interest was typically transcribed with the assistance of a promoter, but ligation to form a circular expression vector is optional. RNA can also be exogenously added or generated without transcription and translated in cell free systems. Configurations of expression constructs for in vitro expression and execution of all of the above expression systems are well within the ability of the skilled artisan.

The above methods of cloning and expression of the *Trichoderma reesei* mannanase gene are suitable both for industrial scale expression and for use in high throughput screens for the evaluation of mutated variants.

Purification: As described above, the mannanase proteins can be expressed in a variety of expression systems and accordingly the appropriate down-stream processing and purification procedures have to be selected. The protein of interest can be secreted into the extracellular or periplasmic space or expressed intracellularly. In an advantageous embodiment of the disclosure the mannanase variant is expressed in a microbial host and the protein is secreted into the periplasmic or extracellular space. Cells expressing the mannanase variants are preserved by methods well known to anyone skilled in the art, such as, but not limited, to cryo stocks. Cultures of the expressing organism are prepared at an appropriate volume with standard methods of fermentation. In a preferred embodiment, cultures for protein expression are inoculated from a cryo stock and the volume of the culture increased successively in the appropriate containers. In a preferred embodiment the cells are grown in a fermenter and optionally growth conditions such as pH, temperature, oxygen and/or nutrient supply are controlled. A first step of purification comprises the separation of cells from supernatant using one or more of several techniques, such as sedimentation, microfiltration, centrifugation, flocculation or other. In a preferred embodiment the method applied is microfiltration. In case of intracellular expression the cells are subjected to treatments that result in a release of the protein from the intracellular space. These treatments may comprise for example pressure, enzymatic, osmotic shock, freezing, ultrasonic or other treatment to produce a cellular extract which may or may not be subjected to further purification.

In an advantageous embodiment of the disclosure the protein is secreted into the supernatant and an optional step of purification comprises the concentration of the supernatant by ultrafiltration. Further protein purification from the supernatant or concentrated supernatant may be performed with one or more of several methods comprising extraction or fractionation methods such as ammonium sulfate or ethanol or acid precipitation, or chromatographic methods including but not limited to ion-exchange, hydrophobic interaction, hydroxylapatite, size fractionation by gel-filtration, phospho-cellulose or lectin chromatography and affinity chromatography or any combination thereof. In a more preferred method the affinity-tagged protein is purified by metal-chelate affinity chromatography to obtain a high purity protein.

The preferred purification method yields a purity of the protein of >30%, in a more preferred method the purity is >50%, >60%, >70%, or >80%. In an even more preferred method the purity is >90%, in a yet more preferred method the purity is >95% and in a most preferred method the purity is >98%.

In another advantageous embodiment of the disclosure the supernatant or the supernatant partially purified by ultra filtration or the concentrated and/or diafiltrated supernatant is dried by any one of several technical methods such as, but not limited to, spray-drying, lyophilisation, down-draught evaporation, thin-layer evaporation, centrifugal evaporation, conveyer drying or any combination thereof.

In a further advantageous embodiment of the disclosure the fermented cell-suspension including the expressed mannanase variants is dried as a whole using processes such as, but not limited to, fluidised bed drying, conveyer drying, spray drying or drum drying or any combination thereof.

Formulations: In general, compositions of the mannanase or any derivative described herein can be either liquid or dry. Liquid compositions may comprise the mannanase alone or in combination with other proteins or enzymes and may contain additives that support the stability and/or activity of the mannanase or other proteins or enzymes in the composition. These include but are not limited to glycerol, sorbitol, propylene glycol, salts, sugars, preservatives, pH-buffers and carbohydrates. Typically, the liquid composition is an aqueous or oil-based slurry, suspension or solution.

Dry compositions may be generated from any liquid composition including the fermentation supernatant or cell suspension or cell extract by spray-drying, lyophilisation, down-draught evaporation, thin-layer evaporation, centrifugal evaporation, conveyer drying or any combination thereof. The dry compositions may be granulates of the appropriate size to be compatible with the further downstream applications such as food or feed processing or to qualify as a component for foods or animal feed.

Before drying a bulking agent may be added to the liquid composition which, after drying, effectively enhances the properties of the dry composition such as providing a higher heat stability due to protection of the enzyme from environmental factors by the bulking reagent, better technical handling properties and others.

Once a dry preparation is obtained, agglomeration granulates may be prepared using agglomeration techniques, e.g. in a shear mixer during which a filler material and the enzyme are co-agglomerated to form granules. Absorption granulates are prepared by having cores of a carrier material to absorb or be coated with the enzyme. Typical filler materials include disodium sulphate, kaolin, talc, magnesium aluminium silicate and cellulose fibres. Optionally, binders such as dextrins are also included in agglomeration granulates. Typical carrier materials include starch, e.g. in form of cassava, corn, potato, rice and wheat, or salts may be used.

Optionally granulates are coated with a coating mixture. Such a mixture comprises coating agents, preferably hydrophobic coating agents, such as hydrogenated palm oil and beef tallow, and, if desired, other additives such as calcium carbonate and kaolin.

In a particularly preferred embodiment the compositions comprising the mannanases of the disclosure are intended for applications in food and feed processing or as supplement to food and feed. In this case, mannanase compositions may additionally contain other substituents such as colouring agents, aroma compounds, stabilizers, vitamins, minerals, other feed or food enhancing enzymes and the like. This applies in particular to the so-called pre-mixes. Food additives according to this present disclosure may be combined with other food components to produce processed food products. Such other food components include one or more other, preferably thermostable, enzyme supplements, vitamin food additives and mineral food additives. The resulting, combined food additive, including possibly several different types of compounds can then be mixed in an appropriate amount with the other food components such as cereal or plant proteins to form a processed food product. Processing of these components into a food product can be performed using any of the currently available methods.

In an advantageous embodiment of the disclosure the mannanase composition additionally comprises an effective amount of one or more feed or food enhancing enzymes, in particular selected from the group consisting of, but not limited to, phytases, hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or others.

Formulations of the mannanases of the disclosure are used for processing and/or manufacturing of food or animal feed.

Technical Applications: Envisioned is the use of the mannanase derivatives as food additives or digestive aids which promote the degradation of oligomannose containing food material, thus releasing potentially beneficial oligomannoses or derivatives thereof.

Another application in the field of food and feed processing is the production of manno-oligosaccharides as important prebiotics from PKE for feed and food. By the treatment of PKE or other galactomannan containing components with mannanase manno-oligosaccharides and D-mannose are produced. Manno-oligosaccharides are used as prebiotic components for feed and food: Manno-oligosaccharides promote the growth of probiotics (e.g. *Bifidobacteria* and *Lactobacillus* sp), inhibit the growth of enterobacteria *Salmonella*, neutralise the antinutritional properties of lectins and find applications in the pharmaceutical industry. Furthermore manno-oligosaccharides and especially mannose are suspected to be immune stimulating components in feed stuff.

Yet another application in the field of food and feed processing is the cleavage of mannan containing components in the cell wall of fruits for juice recovery improvement, e.g. by adding the said enzymes to pineapples, lemons, oranges, limes, grapefruits, prior to the squeezing procedure. An advantageous application is the use of the mannanase variants according to the present disclosure in baking processes e.g. for cookies, bread etc.

Another application in the field of food and feed processing is the use of the mannanase according to the present disclosure for yield improvement in palm kernel oil extraction. The oil content remaining in the palm kernel expeller is between 5-12% after pressing. This remainder can be further reduced by chemical extraction to about 3%. By application of a mannanase according to the disclosure, the release of the fat could be rapidly increased, thus providing an improved process. Additionally the resulting palm kernel expeller would be of higher quality due to the reduced content of galactomannan fibres which are known to be antinutritive components in feed.

Yet another application in the field of food and feed processing is the delivery of D-mannose from PKE or other galactomannan containing components. Palm kernel meal contains about 20% mannose bound as galactomannan fibers. The treatment of PKE, copra or other galactomannan containing raw substances with mannanases causes the release of D-mannose. Mannose and its derivatives are ingredients used in food (e.g. low calorie dietetic food products), pharmaceuticals (mannose cures more than 90% of all urinary tract infections), cosmetics, textiles and in the manufacturing of polymers. Because of limited supply mannose is very expensive at present compared to other more common hexose sugars and its supply is scarce. D-mannose can also be used as a raw material for the production of mannitol. Mannitol itself is derived from Mannose via reduction with much higher yield and less by-products than from the conversion of fructose. Mannitol is a polyol widely used in food and pharmaceutical industries because of its unique functional properties: Mannitol is used as sweetener, for pharmaceutical formulations (chewable tablets and granulated powders), in the production of chewing-gum, as bodying, texturing and anti-caking agent for food, as osmoactive pharmaceutical and diabetic food component.

Furthermore, in the above context of food and feed processing the use of a mannanase according to the disclosure for the partial hydrolysis of galactomannans by incubation of guar gum or locust bean gum is provided. The resulting hydrolysates are used in food and brewery industry as texturing components and for pharmaceutical applications.

Production of Sugars: The described mannanase enzymes in the present disclosure are in particular useful for the production of sugars or oligosaccharides from polymannose containing plant material such as palm kernel, coconut, konjac, locust bean gum, gum guar and soy beans. Preferred is plant material like palm kernel meal, palm kernel expellers, copra meal, copra pellets and soy bean hulls.

In a particular preferred embodiment the mannanase enzymes according to the present disclosure are applied for the production of mannose and mannopolymers such as mannobiose, mannotriose, mannotetraose, mannopentaose, mannohexaose, mannoheptaose, mannooctaose, mannononaose and higher polymers of mannose and/or derivatives thereof. Also preferred are galactosyl mannooligosaccharides thereof with different ratios between galactose and mannose ranging from 1 to 0.05.

In a further preferred embodiment of the present disclosure the sugars are composed of mannose and glucose and are referred to as glucomannans. These polyols might be composed of 2, 3, 4, 5, 6, 7, 8, 9 or more monomers of mannose and/or glucose with a mannose content of 1/15, 1/14, 1/13, 1/12, 1/11, 1/10, 1/9, 1/8, 1/7, 1/6, 1/5, 1/4, 1/3, 1/2, 1, 2/3, 3/4, 3/5, 4/5, 5/6, 2/7, 3/7, 4/7, 5/7, 6/7, 3/8, 5/8, 7/8, 2/9, 4/9, 3/10, 2/11, 4/11, 3/12, 2/13 or 1/14. Also particularly preferred are galactosyl glucomannooligosaccharides thereof with different ratios between galactose and mannose ranging from 1 to 0.05.

In a further preferred embodiment of the present disclosure the mannanase is used in combination with other carbohydrases like glucanase, and/or xylanase, and/or alpha-galactosidase and/or cellulase for the hydrolysis of the plant material in order to generate the sugars.

In a more preferred embodiment of the present disclosure the hydrolysis of the polymannose containing plant material leads to sugars exhibiting a prebiotic functionality. These sugars are generated to promote the growth of probiotics, bacteria that are known to support a healthy immune system. Examples of such bacteria are bifidobacteria. Known bifidoabteria are *B. adolescensis, B. angulatum, B. animalis, B. asteroides, B. bifidum, B. bifidum, B. boum, B. breve, B. catenulatum, B. choerinum, B. coryneforme, B. cuniculi, B. dentium, B. gallicum, B. gallinarum, B. indicum, B. infantis, B. longum, B. magnum, B. merycicum, B. minimum, B. pseudocatenulatum, B. pseudolongum, B. pullorum, B. ruminantium, B. saeculare, B. scardovii, B. subtile, B. thermacidophilum* and *B. thermophilum*.

Coffee Extraction: The described mannanase enzymes according to the present disclosure are useful for the hydrolysis of galactomannan which is present in liquid coffee extracts. In a preferred embodiment of the disclosure the mannanase is used to inhibit the formation of gels as they occur during freeze drying of liquid coffee extracts. The decreased viscosity of the extract reduces the energy consumption during drying. In an even more preferred embodiment of the disclosure the mannanase enzymes are applied in an immobilized form which reduces the consumption of enzyme and prevents contamination of the coffee extract.

In this context, another interesting application is the use of mannanase enzymes according to the present disclosure for the production of mannose or manno-oligosaccharides from coffee waste, in order to receive higher value products. As described before mannanase releases mannose or oligosaccharides from coffee waste which are high value functional feed and food components. In the coffee beverage industry, spent coffee grounds are generally used as fuel or treated as an industrial waste). Roasted coffee contains 1.8-4.4% mannan. Therefore spent coffee grounds contain a large amount of β-mannan, which can be converted into mannooligosaccharides by enzymatic hydrolysis. Mannooligosaccharides obtained from coffee mannan are said to reduce serum lipid levels in humans (Jpn J food eng 6 (2005).

Animal Feed: Several antinutritional factors limit the use of specific plant material in the preparation of animal feed and food for humans. Plant material containing oligomannans like mannan, galactomannan, glucomannan and galactoglucomannan is described to reduce the digestibility and absorption of nutritional compounds like minerals, vitamins, sugars and fats by the animals. The negative effects are in particular due to the high viscosity of the mannopolymers and to the ability of the mannopolymers to adsorb nutritional compounds. These effects can be eliminated/reduced through the use of mannopolymer degrading enzymes, namely mannanase enzymes which then allows a much higher proportion of mannopolymer containing cheap plant material in the feed and thereby a reduction of costs. Additionally, through the activity of the mannanase enzymes mannopolymers are broken down to monosaccharides which can be readily assimilated and provide additional energy. In order to use an enzyme as an effective feed supplement for e.g. monogastric animals like poultry or swine it has to be stable in the stomach. This means it has to be stable at low pH (approx. pH 2-3) and additionally it has to be resistant against pepsin at this low pH. Furthermore such enzymes need to be active at low pH (approx. pH 3.0) to be effective in the stomach. The mannanase enzymes provided in the present disclosure fulfil all these criteria unlike other mannanase enzymes as for example the wild-type mannanase from *Trichoderma reesei* which is not stable at low pH, in particular not stable against pepsin at low pH. Therefore the mannanase enzymes provided in the present disclosure are especially well suited for feed applications in which the enzyme has to be active in the animal. The mannanase enzymes according to the present disclosure are useful as additives to feed for monogastric animals such as poultry and swine, as well as for human food. The feed may however also be provided to ducks, geese, as well as bovine, canine, caprine, equine feline, as well as crustaceans and fish. The mannanase enzymes can also be used to pretreat the feed instead of adding it to the feed.

In an advantageous embodiment of the disclosure the mannanase enzymes are added to feed for weaning pigs, nursery pigs, piglets, fattening pigs, growing pigs, finishing pigs, laying hens, broiler chicks, turkey.

In a further advantageous embodiment of the disclosure the mannanase enzymes are additives to feed composed of plant material like palm kernel, coconut, konjac, locust bean gum, gum guar, soy beans, barley, oats, flax, wheat, corn, linseed, citrus pulp, cottonseed, groundnut, rapeseed, sunflower, peas, lupines and vitamins as well as minerals. In an even more preferred embodiment of the disclosure the mannanase enzymes are additives to feed partially composed of palm kernel meal, palm kernel expellers, copra meal, copra pellets and/or soy bean hulls.

In a further advantageous embodiment of the disclosure the mannanase enzymes are used in combination with other enzymes selected from the group consisting of, but not limited to, phytases, alpha-galactosidases, beta-galactosidases, pectinases, xylanases, arabinoxylanases, proteases, beta-glucanases, cellulases, galactanases, endoglucanases, xylosidases, cutinases, lipases and/or phospholipases for the preparation of feed. The mannanase enzymes with or without additional enzymes can also be used in combination with minerals, vitamins and other typical feed supplements.

Since the mannanase enzymes according to the present disclosure are thermostable enzymes they can be subjected to heat without losing significant activity. Therefore the mannanase enzymes can be used in processes of producing pelleted feed in which heat is applied to the feed mixture before the pelleting step, as it is the case in most commercial pellet mills. The mannanase enzyme can be added to the other feed ingredients in advance to the pelleting step or after the pelleting step to the already formed feed pellets.

In a further preferable embodiment of the present disclosure the mannanase enzymes are used in animal feed that is especially fed to animals under circumstances where no antibiotics are desired.

In an advantageous embodiment the mannanase enzymes are used in animal feed partially composed of palm kernel meal, palm kernel expellers, copra meal, copra pellets and/or soy bean hulls. In a most preferred embodiment the mannanase enzymes are used in animal feed for broiler chicks that is partially composed of palm kernel meal, palm kernel expellers, copra meal, copra pellets and/or soy bean hulls.

Paper Pulp Industry: The mannanase enzymes according to the present disclosure are useful in the enzyme aided bleaching of paper pulps like chemical pulps, semi-chemical pulp, kraft pulps, mechanical pulps or pulps prepared by the sulfite method. The pulps might also be totally chlorine free pulps bleached with oxygen, ozone, peroxide or peroxyacids.

In an advantageous embodiment of the present disclosure the mannanase enzymes are used for the enzyme aided bleaching of pulps produced by modified or continuous pulping methods that exhibit a low lignin contents.

In a further advantageous embodiment of the present disclosure the mannanase enzymes in such applications can either be applied alone or preferably in combination with xylanase and/or endoglucanase and/or alpha-galactosidase and/or cellobiohydrolase enzymes.

Bleaching and/or Desizing Agent in Textile Industry: The mannanase enzymes according to the present disclosure are as well useful for bleaching of non-cotton cellulosic fibers, yarn or fabric comprising flax, jute, ramie or linen by incubation of the fiber, yarn or fabric with a mannanase according to the present disclosure for a given time and under conditions suitable to produce a whitening of the fiber, yarn or fabric. The degradation of hemicellulose improves the bleaching process of the fabric.

In textile printing using a printing paste containing a dye and a biological polymer (e.g. guar gum) as thickener, removal of the thickener and excess dye is made much more efficient by washing the printed textile in the presence of mannanase. The enzymatic breakdown of thickener decreases process time as well as the amount of energy and water needed to achieve a satisfactory quality of the textile.

The mannanase enzymes according to the present disclosure are useful in desizing of fabrics made from e.g. synthetic fibers where often galactomannans like guar gum or locust bean gum are used as sizing agents.

Oil and Gas Well Stimulation by Hydraulic Fracturing:

The mannanase enzymes according to the present disclosure are useful in a method of hydraulic fracturing used in oil or gas well stimulation. Here the mannanase enzymes act as liquefying agents in a hydraulic fluid that is based on or composed of a mannopolymer and usually contains sand.

As the mannanase enzymes according to the present disclosure are thermostable enzymes they are preferably used in hydraulic fracturing applications that are performed at high temperatures.

In another advantageous embodiment of the disclosure the liquefying activity of the mannanase enzymes in a hydraulic fracturing application is controlled (inhibited or promoted) by environmental conditions like pH and temperature.

Detergents: The mannanase enzymes according to the present disclosure can be used in detergent compositions in order to facilitate the removal of mannopolymer containing stains/soils. In a preferred embodiment of the present disclosure the mannanase enzymes are used in detergent compositions in combination with other enzymes from the group of amylases, cellulases, lipases, pectinases, protease and endoglucanases.

Removal of Biofilms: The mannanase enzymes described in the present disclosure are useful for the removal of mannopolymer containing biofilms. Preferably, for such an application the mannanase enzymes are used in combination with detergents and/or other enzymes from the group of alpha-galactosidases, pectinases, xylanases, arabinoxylanases, proteases, beta-glucanases, cellulases, galactanases, endoglucanases, xylosidases, cutinases and lipases.

Delivery Systems: The mannanase enzymes according to the present disclosure can be used for the targeted and/or time-dependent delivery of matter. This is achieved through the use of systems that are based on gels of mannopolymers that contain and transport the matter. The function of the mannanase enzyme in such a system is the controlled release of the matter by partial or complete degradation of the gel, due to a specific change in the environment of the gel, e.g. the pH and/or the temperature that activates the mannanase enzymes.

In an advantageous embodiment of the present disclosure the mannanase enzymes are used for the targeted delivery of a drug in a pharmaceutical application.

Renewable resources, i.e. biomass substrates which are grown and harvested, like crops, straw, wood and wood products, are receiving more and more attention as they are suitable substrates for the production of biological fuels, i.e. solid, liquid, or gas fuel like Biodiesel, Biogas, Vegetable oil, Bioethanol, Biobutanol, BioHydrogen, Bio-Dimethyl ether, Biomethanol, BTL ("Biomass to liquid")-Fuel, GTL ("Gas to liquid")-Fuel, and the like. In 1St generation biological fuels, the said plants have been converted using established methods from the food industry, i.e. they were squeezed in order to obtain vegetable oil or starch containing grain was converted to sugar and subsequently fermented with yeast in order to obtain Bioethanol. This means that the energy reservoirs (i.e. fat and/or starch) of the said plants were utilized exclusively. This led to poor energy yields, or poor production quantities of biofuel per acre. In $2^{nd}$ generation biological fuels, not only the energy reservoirs of the said plants are being used, but the approach tends to utilize the complete biomass of the plant.

In this context, a mannanase according to the disclosure can be used to convert plant biomass containing hemicellulose into sugars, which can be metabolized by specific yeast (e.g. *Saccaromyces* sp.) or bacterial strains and other microorganisms in order to produce fermentation products. These fermentation products can be fuels like Bioethanol, Biobutanol but can also be building block molecules like 3-Hydroxy propionic acid, aspartic acid, xylitol and gluconic acid. For more building block molecules that can be derived from sugars see (Werpy and Petersen (2004) Top Value Added Chemicals from Biomass: Volume 1—Results of Screening for Potential Candidates from Sugars and Synthesis Gas. National Renewable Energy Laboratory Report NREL/TP-510-35523, FIG. 3 and table 8).

Other potential uses comprise the catalytic processing of products which have been obtained from renewable resources with help of mannanases according to the disclosure. This comprises the processing of glucose and/or fructose, both obtained with help of a mannanase according to the disclosure, into 2,5-dimethylfuran, a heterocyclic compound which is supposed to have much better fuel properties than bio ethanol, as it has a 40% greater energy density, is chemically stable and insoluble in water.

The said approaches draw large benefits from the improved properties of the mannanases according to the disclosure, particularly of the enhanced heat stability. This means that the respective biomass to sugar conversion can take place under high temperature conditions, which accelerates the respective processes and thus renders them economically more efficient.

In recent experiments of the inventors, palm-kernel expeller (PKE) substrates were used to feed yeast (*Saccharomyces cerevisiae*). The said substrates contain about 37% galactomannan. It turned out that PKE treated with two mannanases according to the disclosure (i.e., variant B, variant C and/or variant 31) lead to the release of a large amount of sugars, and thus resulted in an improved yeast growth in comparison to untreated PKE. This is a clear hint towards the above postulation, i.e. that the mannanases according to the disclosure may be a useful tool to enhance the yield in e.g. Bioethanol production out of renewable resources (see example 19 in WO 2008/009673).

All the said uses of a mannanase according to the disclosure have in common that these approaches draw substantial benefit from the improved properties of the mannanase according to the disclosure, particularly in terms of enhanced thermostability and enhanced resistance against low pH values and protease enzymes.

This is mainly due to the fact that most of the said uses take place in environments with unfavourable conditions, like in mammalian digestive tracts, where low pH values predominate, or at elevated temperatures which are applied to speed up, facilitate and economically optimise hydrolysis processes like the conversion of renewable resources to sugars as described above.

The following methods and examples are offered for illustrative purposes only, and are not intended to limit the scope of the present disclosure in any way.

METHODS AND EXAMPLES

In the following examples, materials and methods of the present disclosure are provided including the determination of catalytic properties of enzymes obtained by the method. It should be understood that these examples are for illustrative purpose only and are not to be construed as limiting this disclosure in any manner. All publications, patents, and patent applications cited herein are hereby incorporated by reference in their entirety for all purposes.

Example 1

Purification of Mannanase Enzymes Via HisTag

Purification of mannanase enzymes without carbohydrate binding domain (CBD) was performed using a 6×HisTag C-terminally fused to the mannanase enzymes.

*S. saccharomyces*, transformed with a plasmid coding for the 6×His-tagged mannanase, was cultivated in shake flasks at 30° C. for 72 hours in SC-galactose culture medium. Cells from 2 liter culture medium were removed by centrifugation and the supernatant subjected to a 40-fold concentration by ultrafiltration using a 5 kDa cut-off membrane. The concentrate was subsequently diafiltrated with the same cut-off for buffer exchange (50 mM NaH2PO4, 300 mM NaCl, pH 5.0) and concentration to a final volume of ¹⁄₄₀ of the culture volume. The concentrate was filtered through a 0.45 gm filter and the pH adjusted to 8.0 just before loading onto a metal affinity column (BD-Talon, BD-Bioscience). The column was washed with several bed-volumes of diafiltration buffer pH 8.0. Mannanase was eluted with a gradient from 0% to 100% buffer B, whereas buffer B contains 50 mM $NaH_2PO_4$, 300 mM NaCl and 250 mM imidazole at pH 6.0. Eluted protein samples were analyzed by SDS PAGE. Fractions containing mannanase were pooled and dialyzed against buffer containing 50 mM NaOAc, pH 5.0. The purity of mannanase samples was controlled with reversed phase chromatography using absorption at 280 nm for protein detection.

Example 2

Purification of Mannanase Enzymes with C-terminal CBD

Purification of mannanase enzymes with a C-terminal CBD was performed using anion exchange and hydrophobic interaction chromatography. In detail, *S. saccharomyces*, transformed with a plasmid coding for the respective mannanase enzyme, was cultivated in shake flasks at 30° C. for 72 hours in SC-galactose culture medium. Cells from 5 liter culture medium were removed by centrifugation and the supernatant was subjected to concentration and buffer exchange (buffer A: 20 mM Tris(hydroxymethyl)-aminomethan, pH 8.6) by ultrafiltration using a 10 kDa cut-off membrane. Finally 200 ml mannanase concentrate in buffer A was generated. The solution was applied onto a 6.3 ml TSK-gel SuperQ-5PW(30) column (Tosoh Bioscience) equilibrated with buffer A. The column was washed with several column volumes buffer A. Subsequently the mannanase enzyme was eluted with a linear gradient from 0 to 100% buffer B (20 mM Tris(hydroxymethyl)-aminomethan, pH 8.6, 1M NaCl) over 120 ml. Eluted protein samples were analysed by SDS PAGE. Fractions containing mannanase were pooled, diluted 1:1 with a 3M ammonium sulphate solution and loaded on an equilibrated (buffer C: 50 mM NaOAc, pH 5.0, 1.5M ammonium sulphate) 8.8 ml TSK Gel Phenyl-5PW (20) column (Tosoh Bioscience). The column was washed with buffer C. Mannanase elution was performed with a linear gradient from 0 to 100% buffer D (50 mM NaOAc, pH 5.0) over 100 ml. Eluted protein samples were analysed by SDS PAGE. Fractions containing mannanase were pooled and dialyzed against buffer D. Purity of mannanase samples was controlled with reversed phase chromatography using absorption at 280 nm for protein detection.

Example 3

Generation and Characterization of Mannanase Variants

Mannanase variants were generated using different methods for mutagenesis of the DNA encoding the mannanase proteins like cassette or PCR mutagenesis or other mutagenesis methods well known in the art. Those methods comprise such methods as disclosed in Morinaga et al., *Biotechnology* 2:646-649 (1984) and in Nelson and Long, *Analytical Biochemistry* 180:147-151 (1989); or the Error Threshold Mutagenesis protocol described in WO 92/18645. For mutagenic PCR another suitable method is disclosed by Cadwell and Joyce, *PCR Methods Appl.* 3:136-140 (1994).

Mannanase variants were heterologously expressed in one or more of the following expression hosts: *Saccharomyces cerevisiae*, *Bacillus subtilis* and *Escherichia coli*.

Example 4

Determination of Temperature Stability

The temperature stability of mannanase variants is characterized by their inactivation temperatures. The inactivation temperature was determined by measuring the residual activity of the mannanase enzymes after incubation at different temperatures. Residual activities were determined by measuring the mannanase activities with and without prior temperature challenge of the mannanase samples. In more detail, mannanase samples were incubated in 50 mM NaOAc buffer, pH 5.0 and 0.025% Triton-X-100 for 45 mM at various temperatures. Subsequently the mannanase activities were determined using AZCL-galactomannan (carob, Megazyme) as a substrate. For this mannanase samples and a mannanase enzyme calibration series (purified mannanase according to Seq. ID No 3 with a C-terminal 6×HisTag) were incubated with 1 mg/ml AZCL-galactomannan, 50 mM NaOAc, pH 5.0 and 0.1% Triton-X-100 for 60 mM at 37° C. Supernatants from the AZCL-galactomannan assay were subsequently transferred to 96-well microtitre plate and absorption was determined at 590 nm in a standard plate reader. Absorption data for the mannanase enzyme calibration series were plotted against the enzyme concentration. Activities of the other mannanase samples were calculated using equations that were generated by appropriate curve fitting of the data for the mannanase enzyme standard series. Therefore, the activities of the mannanase samples are expressed as activity equivalents of the mannanase enzyme calibration series.

The inactivation temperature of a mannanase enzyme is defined as the temperature at which the residual activity of the mannanase is 50% compared to the residual activity of the same mannanase after incubation under the same conditions but at room temperature. Where appropriate extrapolations and interpolations from the activity data were made in order to determine the temperature corresponding to 50% residual activity. Temperature stability differences (TD) in [° C.] were calculated by subtracting the inactivation temperatures of two enzymes from each other.

TABLE 3

Temperature stability differences (TD) in [° C.] for mannanase variants. The variants presented are based on Seq. ID No 3 and carry C-terminally either a 6xHisTag or carbohydrate binding domain (CBD, Seq. ID No 10, FIG. 11). The substitutions presented were introduced into Seq. ID No 3. Temperature stability difference (TD) is defined as (inactivation temperature of the variant) − (inactivation temperature of Seq. ID No 3) with both the variant and the enzyme with Seq. ID No 3 having the identical C-terminal tag. The enzyme with Seq. ID No 3 carrying a C-terminal CBD exhibits an inactivation temperature of 74.6° C. The enzyme with Seq. ID No3 carrying a C-terminal 6xHisTag exhibits an inactivation temperature of 75.7° C.

| Variant | C-terminal tag | TD/ [° C.] |
|---|---|---|
| F31Y/S66P/Q97R/N113Y/N173H/V181H/A215T/Q259R/Q280R/N282D/N331S | 6xHis | 9.3 |
| S66P/Q97R/N113Y/N173H/V181A/A215T/Q259R/Q280S/N331S | 6xHis | 9.0 |
| F31Y/S66P/Q97R/N173H/V181H/A215T/Q259R/Q280R/N282D | 6xHis | 8.6 |
| F31Y/S66P/Q97R/N173H/V181H/A215T/Q259R/Q280S/N282D/N331S | 6xHis | 8.5 |
| F31Y/S66P/Q97R/N113Y/N173H/V181H/A215T/Q259R/Q280R/N282D | 6xHis | 8.4 |
| F31Y/S66P/Q97R/Q149K/N173H/V181H/A215T/Q259R/Q280L | 6xHis | 8.2 |
| S66P/Q97R/N113Y/N173H/V181A/A215T/Q259R | 6xHis | 8.0 |
| F31Y/S66P/Q97R/N113Y/N173H/V181H/A215T/Q259R/Q280S/N282D/N331S | 6xHis | 7.9 |
| S66P/N113Y/N173H/V181H/A215T/Q259R | 6xHis | 7.9 |
| F31Y/S66P/Q97R/N113Y/K146Q/N173H/V181H/A215T/Q259R/Q280L/N282D | 6xHis | 7.8 |
| F31Y/S66P/Q97R/N113Y/K146Q/N173H/V181A/A215T/Q259R/Q280L/N282D/N331S | 6xHis | 7.7 |
| F31Y/S66P/Q97R/N113Y/K146Q/N173H/V181H/A215T/Q259R/Q280L | 6xHis | 7.6 |
| F31Y/S66P/Q97R/N173H/V181H/A215T/Q259R/N282D | 6xHis | 7.3 |
| F31Y/S66P/Q97R/N113Y/K146Q/N173H/V181A/A215T/Q259R/Q280R/N282D | 6xHis | 7.3 |
| S66P/N113Y/V181H/A215T/Q259R | 6xHis | 7.2 |
| S66P/Q97R/N113Y/N173H/V181H/A215T/Q259R/Q280L/N282D | 6xHis | 7.1 |
| F31Y/S66P/Q97R/N113Y/K146Q/N173H/V181A/A215T/Q259R/Q280L/N282D | 6xHis | 7.0 |
| F31Y/S66P/N173H/V181H/A215T/Q259R/N282D | 6xHis | 6.9 |
| F31Y/S66P/Q97R/N173H/V181H/A215T/Q259R/Q280L | 6xHis | 6.8 |
| S66P/Q97R/N113Y/N173H/V181H/A215T/Q259R/Q280R/N282D | 6xHis | 6.8 |
| F31Y/S66P/Q97R/N113Y/N173T/V181H/A215T/Q259R/Q280R/N282D | 6xHis | 6.7 |
| F31Y/S66P/Q97R/N173T/V181H/A215T/Q259R/Q280R/N282D | 6xHis | 6.7 |
| F31Y/S66P/Q97R/N173H/V181H/A215T/Q259R/Q280S/N282D | 6xHis | 6.5 |
| S66P/N113Y/N173H/V181H/A215T/Q259R/Q280S/N282D | 6xHis | 6.4 |
| S66P/Q97R/N113Y/N173H/V181A/A215T/Q259R/Q280S/N282D/N331S | 6xHis | 6.3 |
| S66P/Q97R/N113Y/V181H/A215T/Q259R/Q280L/N282D | 6xHis | 6.2 |
| S66P/N113Y/N173H/V181H/A215T/Q259R/N331S | 6xHis | 5.9 |
| F31Y/S66P/Q97R/N113Y/K146Q/N173H/V181A/A215T/Q259R/Q280R/N282D/N331S | 6xHis | 5.9 |
| F31Y/S66P/Q97R/N113Y/K146Q/V181H/A215T/Q259R/Q280S/N282D/N331S | 6xHis | 5.3 |
| S66P/Q97R/N113Y/N173T/V181A/A215T/Q259R | 6xHis | 5.2 |
| F31Y/S66P/Q97R/N113Y/K146Q/N173H/V181A/A215T/Q259R/Q280S/N331S | 6xHis | 5.0 |
| F31Y/S66P/Q97R/N113Y/V181H/A215T/Q259R | 6xHis | 5.0 |
| S66P/Q97R/N113Y/N173H/V181A/A215T/Q259R/N331S | 6xHis | 4.7 |
| F31Y/S66P/Q97R/N113Y/V181H/A215T/Q259R/Q280L | 6xHis | 4.7 |
| F31Y/S66P/Q97R/N113Y/K146Q/V181H/A215T/Q259R/Q280L | 6xHis | 4.6 |
| F31Y/S66P/Q97R/K146Q/V181H/A215T/Q259R/Q280R/N282D | 6xHis | 4.6 |
| S66P/N113Y/V181H/A215T/Q259R/N282D | 6xHis | 4.4 |
| F31Y/S66P/Q97R/V181H/A215T/Q259R/N282D | 6xHis | 4.4 |
| S66P/N113Y/N173H/V181H/A215T/Q259R/Q280S/N331S | 6xHis | 4.2 |
| F31Y/S66P/Q97R/N113Y/K146Q/N173H/V181H/A215T/Q259R/Q280S/N331S | 6xHis | 4.1 |
| S66P/V181H/A215T/Q259R/N282D | 6xHis | 4.0 |
| F31Y/S66P/Q97R/N113Y/K146Q/V181H/A215T/Q259R/Q280L/N331S | 6xHis | 3.9 |
| S66P/Q97R/N113Y/N173H/V181H/A215T/Q259R/N282D | 6xHis | 3.8 |

TABLE 3-continued

Temperature stability differences (TD) in [° C.] for mannanase variants. The variants presented are based on Seq. ID No 3 and carry C-terminally either a 6xHisTag or carbohydrate binding domain (CBD, Seq. ID No 10, FIG. 11). The substitutions presented were introduced into Seq. ID No 3. Temperature stability difference (TD) is defined as (inactivation temperature of the variant) − (inactivation temperature of Seq. ID No 3) with both the variant and the enzyme with Seq. ID No 3 having the identical C-terminal tag. The enzyme with Seq. ID No 3 carrying a C-terminal CBD exhibits an inactivation temperature of 74.6° C. The enzyme with Seq. ID No3 carrying a C-terminal 6xHisTag exhibits an inactivation temperature of 75.7° C.

| Variant | C-terminal tag | TD/ [° C.] |
|---|---|---|
| S66P/Q97R/N113Y/V181H/A215T/Q259R/N282D | 6xHis | 3.8 |
| S66P/V181H/A215T/Q259R | 6xHis | 3.7 |
| S66P/Q97R/N113Y/V181H/A215T/Q259R/Q280R/N282D | 6xHis | 3.6 |
| F31Y/S66P/N173T/V181H/A215T/Q259R/N282D | 6xHis | 3.2 |
| S66P/A215T/Q259R | 6xHis | 3.2 |
| F31Y/S66P/N113Y/V181H/A215T/Q259R/Q280R/N344D | 6xHis | 3.1 |
| F31Y/S66P/Q97R/N113Y/N173H/V181H/A215T/Q259R/Q280R/N282D | CBD | 8.0 |
| F31Y/S66P/Q97R/N113Y/N173H/V181H/A215T/Q259R/Q280S/N282D/N331S | CBD | 6.9 |
| S66P/N113Y/N173H/V181H/A215T/Q259R/Q280S | CBD | 6.8 |
| S66P/Q97R/N113Y/N173H/V181A/A215T/Q259R | CBD | 6.7 |
| S66P/Q97R/N113Y/N173H/V181A/A215T/Q259R/Q280S | CBD | 6.4 |
| S66P/N113Y/N173H/V181H/A215T/Q259R/Q280S/N282D | CBD | 6.4 |
| F31Y/S66P/Q97R/N173H/V181H/A215T/Q259R/Q280R/N282D | CBD | 6.3 |
| S66P/N113Y/N173H/V181H/A215T/Q259R | CBD | 5.7 |
| S66P/Q97R/N113Y/N173H/V181A/A215T/Q259R/N331S | CBD | 5.2 |
| F31Y/S66P/Q97R/N173H/V181H/A215T/Q259R/Q280S/N282D/N331S | CBD | 5.2 |
| S66P/N113Y/N173H/V181H/A215T/Q259R/Q280S/N331S | CBD | 5.1 |
| S66P/Q97R/N113Y/N173H/V181A/A215T/Q259R/Q280S/N331S | CBD | 4.3 |
| F31Y/S66P/Q97R/Q149K/N173H/V181H/A215T/Q259R/Q280S/N331S | CBD | 4.0 |

Example 5

Specific Activity

The specific activity of mannanase enzymes was determined using the purified enzymes according to examples 1 and 2. Mannanase activity was defined as liberation of reducing sugars from galactomannan. Mannanase protein was determined by optical density (OD) measurements at 280 nm.

In detail, purified mannanase samples were diluted in 50 mM NaOAc, pH 5.0. A galactomannan carob (low viscosity, Megazyme) solution was added to yield final concentrations of 0.7% (w/v) galactomannan, 50 mM NaOAc, pH 5.0 and approx. 10 µg/ml mannanase protein. The solutions were incubated for 16 hours at 37° C.

Subsequently the amount of reducing sugar was determined as follows. One part of the galactomannan assay or defined mannose solutions was mixed with one part of a solution containing 1% (w/v) dinitrosalicylic acid (DNSA), 30% (w/v) potassium sodium tartrate and 0.4 M NaOH. The mixture was incubated for 10 min at 99° C. and 5 min a 4° C. Finally the absorption was measured at 540 nm. Reducing sugar equivalents (as mannose equivalents) were calculated by plotting the absorption data for the mannose standard samples against the mannose concentration. The amount of reducing sugar equivalents for the samples was calculated using equations that were generated by appropriate curve fitting of the data for the mannose standard samples.

Mannanase concentrations were calculated from the optical density of the preparations at 280 nm and the respective extinction coefficient for each mannanase variant. The extinction coefficients were calculated on the basis of the amino acid composition of the proteins according to a method provided by Gill and von Hippel, *Analytical Biochemistry* 182: 319-326 (1989).

The specific activity of the mannanase enzymes according to the present disclosure is expressed in nkat per mg mannanase protein on the substrate galactomannan carob, as described above. An activity of one nkat is defined as the liberation of one nanomole reducing sugars per second.

TABLE 4

Specific activity of mannanase variants. The variants presented are based on Seq. ID No 3 and carry C-terminally either a 6xHisTag or carbohydrate binding domain (CBD, Seq. ID No 10). The substitutions presented were introduced into Seq. ID No 3. The specific activity values are defined as (specific activity of the variant)/(specific activity of the reference). The reference in this case is the mannanase from Seq. ID No 3 with the same C-terminal tag as present in the respective variant. The reference with a C-terminal 6xHisTag has a specific activity of 1228 nkat/mg and the reference with a C-terminal CBD has a specific activity of 535 nkat/mg.

| Variant | C-terminal tag | Specific activity [% reference] | Specific activity [nkat/mg] |
|---|---|---|---|
| F31Y/S66P/Q97R/N113Y/N173H/V181H/A215T/Q259R/Q280R/N282D | 6xHis | 107 | 1064 |
| S66P/Q97R/N113Y/N173H/V181A/A215T/Q259R | 6xHis | 119 | 1184 |
| S66P/N113Y/N173H/V181H/A215T/Q259R | 6xHis | 173 | 1529 |
| F31Y/S66P/Q97R/N113Y/N173H/V181H/A215T/Q259R/N282D | 6xHis | 167 | 1482 |
| F31Y/S66P/Q97R/N113Y/N173H/V181H/A215T/Q259R/Q280R/N282D | CBD | 144 | 872 |
| F31Y/S66P/Q97R/N173H/V181H/A215T/Q259R/Q280R/N282D | CBD | 112 | 679 |
| S66P/N113Y/N173H/V181H/A215T/Q259R | CBD | 212 | 1008 |
| F31Y/S66P/Q97R/N173H/V181H/A215T/Q259R/Q280S/N282D/N331S | CBD | 141 | 756 |

TABLE 4-continued

Specific activity of mannanase variants. The variants presented are based on Seq. ID No 3 and carry C-terminally either a 6xHisTag or carbohydrate binding domain (CBD, Seq. ID No 10). The substitutions presented were introduced into Seq. ID No 3. The specific activity values are defined as (specific activity of the variant)/(specific activity of the reference). The reference in this case is the mannanase from Seq. ID No 3 with the same C-terminal tag as present in the respective variant. The reference with a C-terminal 6xHisTag has a specific activity of 1228 nkat/mg and the reference with a C-terminal CBD has a specific activity of 535 nkat/mg.

| Variant | C-terminal tag | Specific activity [% reference] | Specific activity [nkat/mg] |
|---|---|---|---|
| F31Y/S66P/Q97R/Q149K/N173H/V181H/A215T/Q259R/Q280S/N331S | CBD | 149 | 813 |

Example 6

Low pH/pepsin Stability

For the determination of low pH/pepsin stability of the mannanase enzymes, *S. saccharomyces*, transformed with a plasmid coding for the respective mannanase enzyme, was cultivated in shake flasks at 30° C. for 72 hours in SC-galactose culture medium. Cells were removed by centrifugation and the supernatant was separated and concentrated, e.g. 10-fold by ultrafiltration with 10 kDa cut-off membranes. Concentrated supernatants were diluted, e.g. 10-fold in an autoclaved solution containing 30 g/l potato fruit water, 30 g/l corn steep liquor, 5 g/l ammonium sulphate, 15 g/l $KH_2PO_4$, 10 g/l locus bean gum and 20 g/l cellulose (Avicell). Diluted mannanase samples were mixed 1:1 with pepsin assay (200 mM glycine-HCl, pH1.5, 5 mg/ml pepsin-pre-digested BSA, 2 mM $CaCl_2$ and 0.5 mg/ml pepsin) and incubated for 2 hours at 37° C. The pH of the mixture was pH 2.45. In addition a control sample was generated. For this the same diluted mannanase samples were mixed 1:1 with control assay (100 mM NaOAc, pH 5.2, 5 mg/ml pepsin-pre-digested BSA and 2 mM $CaCl_2$) and incubated for 2 hours at 37° C. The pH of the mixture was pH 5.2.

For mannanase activity determination, 1 part of the above mixtures or of a mannanase enzyme calibration series (purified mannanase according to Seq. ID No 3 with a C-terminal 6xHisTag) are mixed with 14 parts AZCL-galactomannan assay (200 mM NaOAc, pH 5.0, 0.1% Triton-X-100, 1% AZCL-galactomannan carob (Megazyme)) and incubated for 60 min at 37° C. Samples are centrifuged and supernatants analyzed for absorption at 590 nm. Absorption data for the mannanase enzyme calibration series were plotted against the enzyme concentration. Activities of the other mannanase samples were calculated using equations that were generated by appropriate curve fitting of the data for the mannanase enzyme calibration series. Therefore, the activities of the mannanase samples are expressed as activity equivalents of the mannanase enzyme calibration series.

Residual activities of mannanase enzymes are calculated as the following ratio:

(Mannanase activity after incubation in pepsin assay)/(mannanase activity after incubation in control assay).

TABLE 5

Low pH/pepsin stability of mannanase variants. The variants presented are based on Seq. ID No 3 and carry C-terminally a carbohydrate binding domain (CBD, Seq. ID No 10). The substitutions presented were introduced into Seq. ID No 3. The reference mannanase according to Seq. ID No 1 with a C-terminal CBD exhibits a residual activity of 39%.

| Variant | C-terminal tag | pH/pepsin stability/ [% residual activity] |
|---|---|---|
| F31Y/S66P/Q97R/N113Y/N173H/V181H/A215T/Q259R/Q280R/N282D | CBD | 96 |
| F31Y/S66P/Q97R/N173H/V181H/A215T/Q259R/Q280R/N282D | CBD | 74 |
| S66P/N113Y/N173H/V181H/A215T/Q259R | CBD | 68 |
| F31Y/S66P/Q97R/N173H/V181H/A215T/Q259R/Q280S/N282D/N331S | CBD | 75 |
| F31Y/S66P/Q97R/Q149K/N173H/V181H/A215T/Q259R/Q280S/N331S | CBD | 63 |

Example 7

Comparison of *Trichoderma reesei* Mannanase and the Variant S3R

The temperature stability and mannose production of *Trichoderma reesei* mannanase as shown in SEQ ID NO:1 was compared with the mannanase variant derived from SEQ ID NO:1 by introducing the substitution S3R (serine to arginin at position 3). The experiment and the results are described in detail in WO 2008/009673 (example 8, p. 100-101; FIG. 1B) and in FIG. 10.

Sequence Listing, Free Text
SEQ ID NO 1: fragment of wild-type *Trichoderma reesei* mannanase/amino-acid
SEQ ID NO 2: mannanase variant V-31 disclosed in WO 2008/009673/amino-acid
SEQ ID NO 3: mannanase variant V-31/S3R disclosed in WO 2008/009673/amino-acid
SEQ ID NO 4: mannanase variant TM-1/amino-acid
SEQ ID NO 5: mannanase variant TM-1/DNA
SEQ ID NO 6: mannanase TM-100/amino-acid
SEQ ID NO 7: mannanase variant TM-108/amino-acid
SEQ ID NO 8: mannanase variant TM-CBD-148/amino-acid
SEQ ID NO 9: mannanase variant TM-144/amino-acid
SEQ ID NO 9: CBD/amino-acid

The invention claimed is:

1. A mannanase variant having mannanase activity and an amino acid sequence that varies from the amino acid sequence of parent/wild type *Trichoderma reesei* mannanase (SEQ ID NO: 1), wherein the amino acid sequence of the mannanase variant comprises the variations 3R, 201S, 207F and 274L, and variations 66P, 215T and 259R and a sequence identity of at least 90% to SEQ ID NO: 1.

2. The mannanase variant of claim 1, wherein the mannanase variant comprises the variation 181A/H.

3. The mannanase variant of claim 1, wherein the mannanase variant further comprises one or more additional variations at positions 31, 97, 113, 146, 149, 173, 181, 280, 282, 331 or 344.

4. The mannanase variant of claim 3, wherein the variations are 3IY, 97R, 113Y, 146Q, 149K, 173H/T, 181H/A, 280S/L/R, 282D, 331S or 344D.

5. A composition which is suitable for food and feed processing, as supplement to food and feed, for enzyme aided bleaching of paper pulps, for oil and gas well stimulation by hydraulic fracturing, as detergent, for removal of biofilms, or in delivery systems comprising the mannanase variant according to claim 1.

6. A composition comprising the mannanase variant according to claim 1 and one or more enzymes selected from the group consisting of phytases, hemicellulases, alpha-galactosidases, beta-galactosidases, lactases, beta-glucanases, endo-beta-1,4-glucanases, cellulases, xylosidases, xylanases, xyloglucanases, xylan acetylesterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, and cutinases.

7. A food or feed supplement which comprises the mannanase variant of claim 1.

8. A detergent comprising the mannanase variant of claim 1.

9. A bleaching or desizing agent for textiles comprising the mannanase variant of claim 1.

10. A method for preparing coffee extract, comprising adding the mannanase variant of claim 1 in a liquid coffee extract, and freeze drying the liquid coffee extract.

11. A method of processing coffee waste, the method comprising adding the mannanase variant of claim 1 to spent coffee grounds.

12. A method of bleaching paper pulps, the method comprising adding the mannanase variant of claim 1 to paper pulp under conditions suitable to produce a whitening of the pulp.

13. A method of removing biofilms, the method comprising contacting the biofilm with the mannanase variant of claim 1, resulting in removal of the biofilm.

14. A mannanase variant having mannanase activity and an amino acid sequence that varies from the amino acid sequence of parent/wild type Trichoderma reesei mannanase (SEQ ID NO:1, wherein the amino acid sequence of the mannanase variant comprises the variations 3R, 201S, 207F and 274L, and further variations selected from the group consisting of:
1) F31Y/S66P/Q97R/N113Y/N173H/V181H/A215T/Q259R/Q280R/N282D/N331S;
2) S66P/Q97R/N113Y/N173H/V181A/A215T/Q259R/Q280S/N331S;
3) F31Y/S66P/Q97R/N173H/V181H/A215T/Q259R/Q280R/N282D;
4) F31Y/S66P/Q97R/N173H/V181H/A215T/Q259R/Q280S/N282D/N331S;
5) F31Y/S66P/Q97R/N113Y/N173H/V181H/A215T/Q259R/Q280R/N282D;
6) F31Y/S66P/Q97R/Q149K/N173H/V181H/A215T/Q259R/Q280L;
7) S66P/Q97R/N113Y/N173H/V181A/A215T/Q259R;
8) F31Y/S66P/Q97R/N113Y/N173H/V181H/A215T/Q259R/Q280S/N282D/N331S;
9) S66P/N113Y/N173H/V181H/A215T/Q259R;
10) F31Y/S66P/Q97R/N113Y/K146Q/N173H/V181H/A215T/Q259R/Q280L/N28 2D;
11) F31Y/S66P/Q97R/N113Y/K146Q/N173H/V181A/A215T/Q259R/Q280L/N28 2D/ N331S;
12) F31Y/S66P/Q97R/N113Y/K146Q/N173H/V181H/A215T/Q259R/Q280L;
13) F31Y/S66P/Q97R/N173H/V181H/A215T/Q259R/N282D;
14) F31Y/S66P/Q97R/N113Y/K146Q/N173H/V181A/A215T/Q259R/Q280R/N28 2D;
15) S66P/N113Y/V181H/A215T/Q259R;
16) S66P/Q97R/N113Y/N173H/V181H/A215T/Q259R/Q280L/N282D;
17) F317/S66P/Q97R/N113YNK146Q/N173H/V181A/A215T/Q259R/Q280L/N28 2D;
18) F31Y/S66P/N173H/V181H/A215T/Q259R/N282D;
19) F31Y/S66P/Q97R/N173H/V181H/A215T/Q259R/Q280L;
20) S66P/Q97R/N113Y/N173H/V181H/A215T/Q259R/Q280R/N282D;
21) F31Y/S66P/Q97R/N113Y/N173T/V181H/A215T/Q259R/Q280R/N282D;
22) F31Y/S66P/Q97R/N173T/V181H/A215T/Q259R/Q280R/N282D;
23) F31Y/S66P/Q97R/N113Y/N173H/V181H/A215T/Q259R/Q280S/N282D;
24) S66P/N113Y/N173H/V181H/A215T/Q259R/Q280S/N282D;
25) S66P/Q97R/N113Y/N173H/V181A/A215T/Q259R/Q280S/N282D/N331S;
26) S66P/Q97R/N113Y/V181H/A215T/Q259R/Q280L/N282D;
27) S66P/N113Y/N173H/V181H/A215T/Q259R/N331S;
28) F31Y/S66P/Q97R/N113Y/K146Q/N173H/V181A/A215T/Q259R/Q280R/N28 2D/ N331S;
29) F31Y/S66P/Q97R/N113Y/K146Q/V181H/A215T/Q259R/Q280S/N282D/N33 1S;
30) S66P/Q97R/N113Y/N173T/V181A/A215T/Q259R;
31) F31Y/S66P/Q97R/N113Y/K146Q/N173H/V181A/A215T/Q259R/Q280S/N33 1S;
32) F31Y/S66P/Q97R/N113Y/V181H/A215T/Q259R;
33) S66P/Q97R/N113Y/N173H/V181A/A215T/Q259R/N331S;
34) F31Y/S66P/Q97R/N113Y/V181H/A215T/Q259R/Q280L;
35) F31Y/S66P/Q97R/N113Y/K146Q/V181H/A215T/Q259R/Q280L;
36) F31Y/S66P/Q97R/K146Q/V181H/A215T/Q259R/Q280R/N282D;
37) S66P/N113Y/V181H/A215T/Q259R/N282D;
38) F31Y/S66P/Q97R/V181H/A215T/Q259R/N282D;
39) S66P/N113Y/N173H/V181H/A215T/Q259R/Q280S/N331S;
40) F31Y/S66P/Q97R/N113Y/K146Q/N173H/V181H/A215T/Q259R/Q280S/N33 1S;
41) S66P/V181H/A215T/Q259R/N282D;
42) F31Y/S66P/Q97R/N113Y/K146Q/V181H/A215T/Q259R/Q280L/N331S;
43) S66P/Q97R/N113Y/N173H/V181H/A215T/Q259R/N282D;
44) S66P/Q97R/N113Y/V181H/A215T/Q259R/N282D;
45) S66P/V181H/A215T/Q259R;
46) S66P/Q97R/N113Y/V181H/A215T/Q259R/Q280R/N282D;
47) F31Y/S66P/N173T/V181H/A215T/Q259R/N282D;
48) F31Y/S66P/N113Y/V181H/A215T/Q259R/Q280R/N344D;
49) F31Y/S66P/Q97R/N113Y/N173H/V181H/A215T/Q259R/Q280R/N282D;
50) F31Y/S66P/Q97R/N113Y/N173H/V181H/A215T/Q259R/Q280S/N282D/N33 1S;
51) S66P/N113Y/N173H/V181H/A215T/Q259R/Q280S;
52) S66P/Q97R/N113Y/N173H/V181A/A215T/Q259R;
53) S66P/Q97R/N113Y/N173H/V181A/A215T/Q259R/Q280S;
54) S66P/N113Y/N173H/V181H/A215T/Q259R/Q280S/N282D;
55) F31Y/S66P/Q97R/N173H/V181H/A215T/Q259R/Q280R/N282D;
56) S66P/N113Y/N173H/V181H/A215T/Q259R;
57) S66P/Q97R/N113Y/N173H/V181A/A215T/Q259R/N331S;
58) F31Y/S66P/Q97R/N173H/V181H/A215T/Q259R/Q280S/N282D/N331S;
59) S66P/N113Y/N173H/V181H/A215T/Q259R/Q280S/N331S;
60) S66P/Q97R/N113Y/N173H/V181A/A215T/Q259R/Q280S/N331S;
61) F31Y/S66P/Q97R/Q149K/N173H/V181H/A215T/Q259R/Q280S/N331S; and
62) S66P/A215T/Q259R,
and wherein the mannanase variant has a sequence identity of at least 90% to SEQ ID NO: 1.

* * * * *